United States Patent
Riley et al.

(10) Patent No.: US 10,610,679 B2
(45) Date of Patent: Apr. 7, 2020

(54) ECG AND DEFIBRILLATOR ELECTRODE DETECTION AND TRACKING SYSTEM AND METHOD

(71) Applicant: ZOLL Medical Corporation, Chelmsford, MA (US)

(72) Inventors: Michael J. Riley, Chelmsford, MA (US); Gary A. Freeman, Chelmsford, MA (US); Frederick J. Geheb, Chelmsford, MA (US); Annemarie E. Silver, Chelmsford, MA (US); Lisa M. Campana, Chelmsford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 621 days.

(21) Appl. No.: 15/083,044

(22) Filed: Mar. 28, 2016

(65) Prior Publication Data
US 2016/0279405 A1    Sep. 29, 2016

Related U.S. Application Data

(60) Provisional application No. 62/139,488, filed on Mar. 27, 2015.

(51) Int. Cl.
*A61N 1/04* (2006.01)
*A61N 1/39* (2006.01)
(Continued)

(52) U.S. Cl.
CPC ............ *A61N 1/046* (2013.01); *A61B 5/0408* (2013.01); *A61B 5/721* (2013.01); *A61B 5/743* (2013.01);
(Continued)

(58) Field of Classification Search
CPC .............. A61H 31/005; A61H 2230/04; A61H 2201/5058; A61H 31/00;
(Continued)

(56) References Cited

U.S. PATENT DOCUMENTS 4,059,099 A    11/1977 Davis
4,088,138 A    5/1978 Diack et al.
(Continued)

FOREIGN PATENT DOCUMENTS

WO    2016160726 A1    10/2015

OTHER PUBLICATIONS

US 6,303,107 B1, 10/2001, Myklebust et al. (withdrawn)
(Continued)

*Primary Examiner* — Jack Yip
(74) *Attorney, Agent, or Firm* — Finch & Maloney PLLC

(57) ABSTRACT

A system and method for aiding in the proper placement of ECG electrodes and other resuscitation parameters. The system includes motion sensors disposed on the ECG electrodes, and a defibrillator control system operable to interpret motion signals from the motions sensors to determine that an electrode is in motion, and thus being handled by rescuer setting up the system for use, and, based on this determination, prompt the rescuer to place the electrode in its intended location on the body of the patient. The control system may also be operable to determine relative motion and/or orientation of the motion sensors and control resuscitation based on the relative motion and/orientation of the motion sensors.

26 Claims, 13 Drawing Sheets

(51) Int. Cl.
  *A61B 5/0408*  (2006.01)
  *A61B 5/00*  (2006.01)
  *G16H 20/30*  (2018.01)
  *G16H 50/20*  (2018.01)
  *G16H 40/63*  (2018.01)
  *G16H 40/40*  (2018.01)
  *A61H 31/00*  (2006.01)

(52) U.S. Cl.
  CPC ......... *A61N 1/3925* (2013.01); *A61N 1/3993* (2013.01); *G16H 20/30* (2018.01); *G16H 40/40* (2018.01); *G16H 40/63* (2018.01); *G16H 50/20* (2018.01); *A61H 31/005* (2013.01); *A61H 31/007* (2013.01); *A61H 2201/10* (2013.01); *A61H 2201/1619* (2013.01); *A61H 2201/1685* (2013.01); *A61H 2201/5007* (2013.01); *A61H 2201/5015* (2013.01); *A61H 2201/5025* (2013.01); *A61H 2201/5043* (2013.01); *A61H 2201/5048* (2013.01); *A61H 2201/5058* (2013.01); *A61H 2201/5064* (2013.01); *A61H 2201/5079* (2013.01); *A61H 2201/5084* (2013.01); *A61H 2230/04* (2013.01); *A61H 2230/045* (2013.01)

(58) Field of Classification Search
  CPC .......... A61H 2201/5064; A61H 31/007; A61H 2201/10; A61H 2201/1619; A61H 2201/1685; A61H 2201/5007; A61H 2201/5015; A61H 2201/5025; A61H 2201/5043; A61H 2201/5048; A61H 201/5079; A61H 2201/5084; A61H 2230/045; A61N 1/39; A61N 1/3925; A61N 1/3987; A61N 1/046; A61N 1/3993; A61B 5/0205; A61B 5/0402; G09B 23/288; G16H 20/30; G16H 50/20; G16H 40/40; G16H 40/63
  USPC ......................................................... 434/265
  See application file for complete search history.

(56) References Cited

U.S. PATENT DOCUMENTS

| | | |
|---|---|---|
| RE30,372 E | 8/1980 | Mirowski et al. |
| 4,296,755 A | 10/1981 | Judell |
| 4,355,634 A | 10/1982 | Kanter |
| 4,588,383 A | 5/1986 | Parker et al. |
| 4,610,254 A | 9/1986 | Morgan et al. |
| 4,619,265 A | 10/1986 | Morgan et al. |
| 4,680,708 A | 7/1987 | Ambos et al. |
| 4,863,385 A | 9/1989 | Pierce |
| 4,928,674 A | 5/1990 | Halperin et al. |
| 5,077,667 A | 12/1991 | Brown et al. |
| 5,092,341 A | 3/1992 | Kelen |
| 5,109,862 A | 5/1992 | Kelen et al. |
| 5,137,458 A * | 8/1992 | Ungs .................. G09B 23/288 434/262 |
| 5,247,945 A | 9/1993 | Heinze et al. |
| 5,285,792 A | 2/1994 | Sjoquist et al. |
| RE34,800 E | 11/1994 | Hutchins |
| 5,391,187 A | 2/1995 | Freeman |
| 5,466,244 A | 11/1995 | Morgan |
| 5,474,574 A | 12/1995 | Payne et al. |
| 5,496,257 A | 3/1996 | Kelly |
| 5,511,553 A | 4/1996 | Segalowitz |
| 5,562,710 A | 10/1996 | Olsen et al. |
| 5,589,639 A | 12/1996 | Antonio et al. |
| 5,591,213 A | 1/1997 | Morgan |
| 5,611,815 A | 3/1997 | Cole et al. |
| 5,617,853 A | 4/1997 | Morgan |
| 5,619,265 A | 4/1997 | Suzuki et al. |
| 5,645,571 A | 7/1997 | Olson et al. |
| 5,662,690 A | 9/1997 | Cole et al. |
| 5,683,424 A | 11/1997 | Brown et al. |
| 5,700,281 A | 12/1997 | Brewer et al. |
| 5,735,879 A | 4/1998 | Gliner et al. |
| 5,755,671 A | 5/1998 | Albrecht et al. |
| 5,957,856 A | 9/1999 | Weil et al. |
| 6,125,299 A | 9/2000 | Groenke et al. |
| 6,171,257 B1 | 1/2001 | Weil et al. |
| 6,174,295 B1 | 1/2001 | Cantrell et al. |
| 6,178,357 B1 | 1/2001 | Gliner et al. |
| 6,201,992 B1 | 3/2001 | Freeman |
| 6,224,562 B1 | 5/2001 | Lurie et al. |
| 6,246,907 B1 | 6/2001 | Lin et al. |
| 6,263,238 B1 | 7/2001 | Brewer et al. |
| 6,308,094 B1 | 10/2001 | Shusterman et al. |
| 6,351,671 B1 | 2/2002 | Myklebust et al. |
| 6,390,996 B1 | 5/2002 | Halperin et al. |
| 6,393,316 B1 | 5/2002 | Gillberg et al. |
| 6,418,342 B1 | 7/2002 | Owen et al. |
| 6,427,685 B1 | 8/2002 | Ray |
| 6,438,419 B1 | 8/2002 | Callaway et al. |
| 6,496,731 B1 | 12/2002 | Lovett |
| 6,597,943 B2 | 7/2003 | Taha et al. |
| 6,658,290 B1 | 12/2003 | Lin et al. |
| 6,671,545 B2 | 12/2003 | Fincke |
| 6,687,540 B2 | 2/2004 | Marcovecchio |
| 6,827,695 B2 | 7/2004 | Palazzolo |
| 6,872,080 B2 | 3/2005 | Pastrick et al. |
| 6,961,612 B2 | 11/2005 | Elghazzawi et al. |
| 7,220,235 B2 | 5/2007 | Geheb |
| 7,570,993 B2 | 8/2009 | Weil et al. |
| 7,993,290 B2 | 8/2011 | Lund et al. |
| 8,034,006 B2 | 10/2011 | Celik-Butler et al. |
| 8,333,720 B2 | 12/2012 | Nysaether |
| 8,394,040 B2 | 3/2013 | Strand et al. |
| 8,532,765 B2 | 9/2013 | Ochs et al. |
| 8,876,742 B2 | 11/2014 | Centen et al. |
| 2001/0047140 A1 | 11/2001 | Freeman |
| 2002/0026131 A1 | 2/2002 | Halperin |
| 2002/0047140 A1 | 4/2002 | Moller et al. |
| 2002/0055694 A1 | 5/2002 | Halperin et al. |
| 2002/0165471 A1 | 11/2002 | Halperin et al. |
| 2002/0165585 A1 | 11/2002 | Dupelle et al. |
| 2002/0193711 A1 | 12/2002 | Halperin et al. |
| 2003/0109790 A1* | 6/2003 | Stickney .............. A61B 5/0809 600/500 |
| 2004/0116969 A1* | 6/2004 | Owen ................ A61B 5/02416 607/6 |
| 2005/0137929 A1 | 6/2005 | Frazier |
| 2006/0111749 A1* | 5/2006 | Westenskow ......... A61M 16/00 607/5 |
| 2006/0116724 A1* | 6/2006 | Snyder .................... A61N 1/39 607/5 |
| 2006/0173498 A1* | 8/2006 | Banville ................. A61N 1/39 607/5 |
| 2006/0173499 A1* | 8/2006 | Hampton ............. A61N 1/3925 607/5 |
| 2006/0173500 A1* | 8/2006 | Walker ................. A61B 5/046 607/5 |
| 2007/0213775 A1* | 9/2007 | Snyder ................ A61N 1/3987 607/7 |
| 2007/0219588 A1* | 9/2007 | Freeman ............. A61H 31/005 607/5 |
| 2008/0004663 A1* | 1/2008 | Jorgenson .......... A61N 1/37247 607/5 |
| 2008/0058656 A1 | 3/2008 | Costello et al. |
| 2008/0103402 A1* | 5/2008 | Stickney .............. A61B 5/0402 600/509 |
| 2008/0312524 A1 | 12/2008 | Solosko et al. |
| 2009/0035740 A1* | 2/2009 | Reed ................... G09B 23/288 434/265 |
| 2009/0306525 A1* | 12/2009 | Pinter ................... G16H 40/67 600/500 |
| 2010/0022886 A1* | 1/2010 | Ayati ................... A61B 5/6822 600/454 |
| 2010/0022904 A1* | 1/2010 | Centen ................ A61H 31/005 600/534 |

(56) References Cited

U.S. PATENT DOCUMENTS

| | | | |
|---|---|---|---|
| 2010/0049266 A1* | 2/2010 | Ochs | A61H 31/005 607/5 |
| 2010/0228166 A1* | 9/2010 | Centen | A61H 31/004 601/41 |
| 2010/0234908 A1* | 9/2010 | Didon | A61N 1/39 607/5 |
| 2011/0118800 A1* | 5/2011 | Sullivan | A61B 5/0452 607/5 |
| 2011/0184759 A1 | 7/2011 | Selker | |
| 2012/0083720 A1 | 4/2012 | Centen et al. | |
| 2012/0123224 A1 | 5/2012 | Packer | |
| 2012/0220887 A1 | 8/2012 | Fossan | |
| 2013/0023781 A1 | 1/2013 | Freeman et al. | |
| 2013/0053649 A1* | 2/2013 | Elghazzawi | A61N 1/39 600/300 |
| 2013/0102936 A1* | 4/2013 | Halsne | A61H 31/005 601/41 |
| 2015/0018823 A1 | 1/2015 | Centen | |
| 2015/0265845 A1* | 9/2015 | Sullivan | A61B 5/7405 607/8 |
| 2015/0297107 A1* | 10/2015 | Sullivan | A61B 5/04 600/523 |

OTHER PUBLICATIONS

International Search Report and Written Opinion issued in PCT/US2014/036887, dated Oct. 3, 2014, 14 pages.
International Search Report and Written Opinion issued in PCT/US2016/024563, dated Jul. 1, 2016, 12 pages.
International Preliminary Report on Patentability received for PCT/US2016/024563, dated Oct. 3, 2017. 11 pages.

* cited by examiner

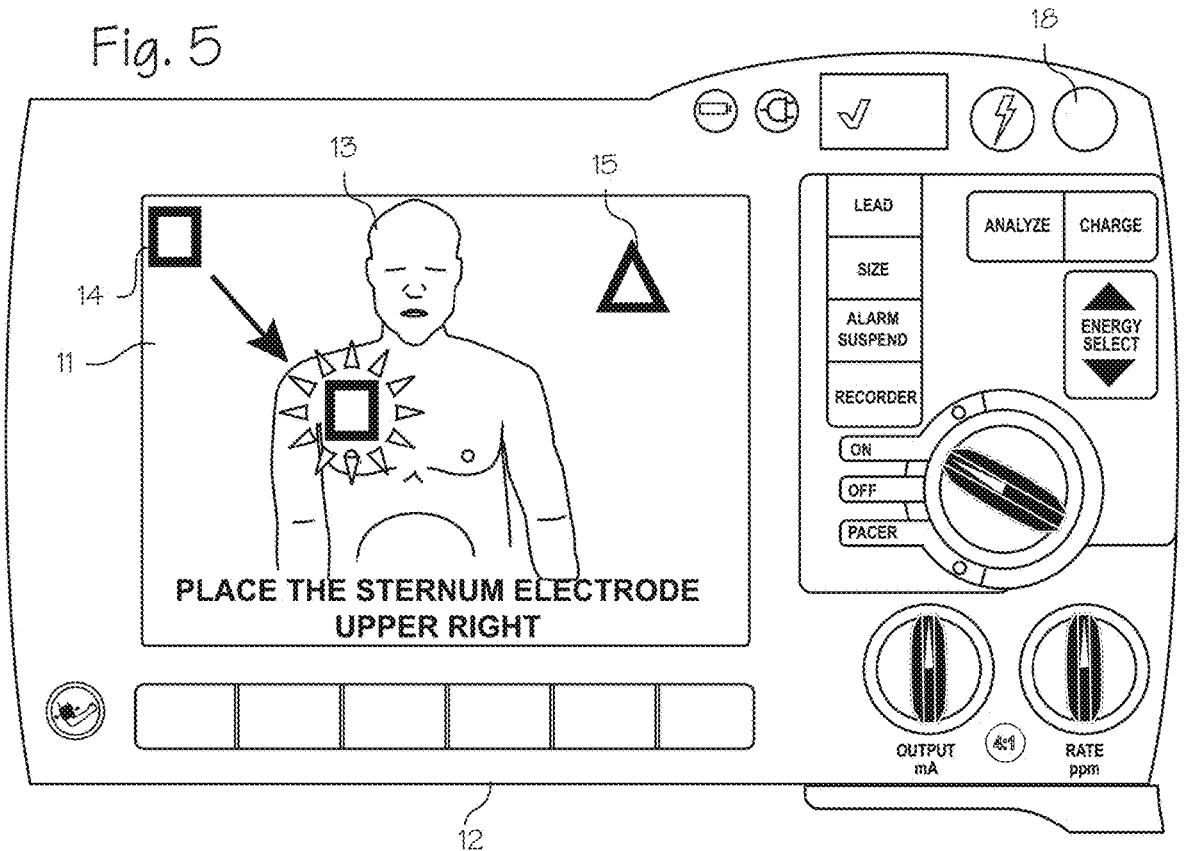
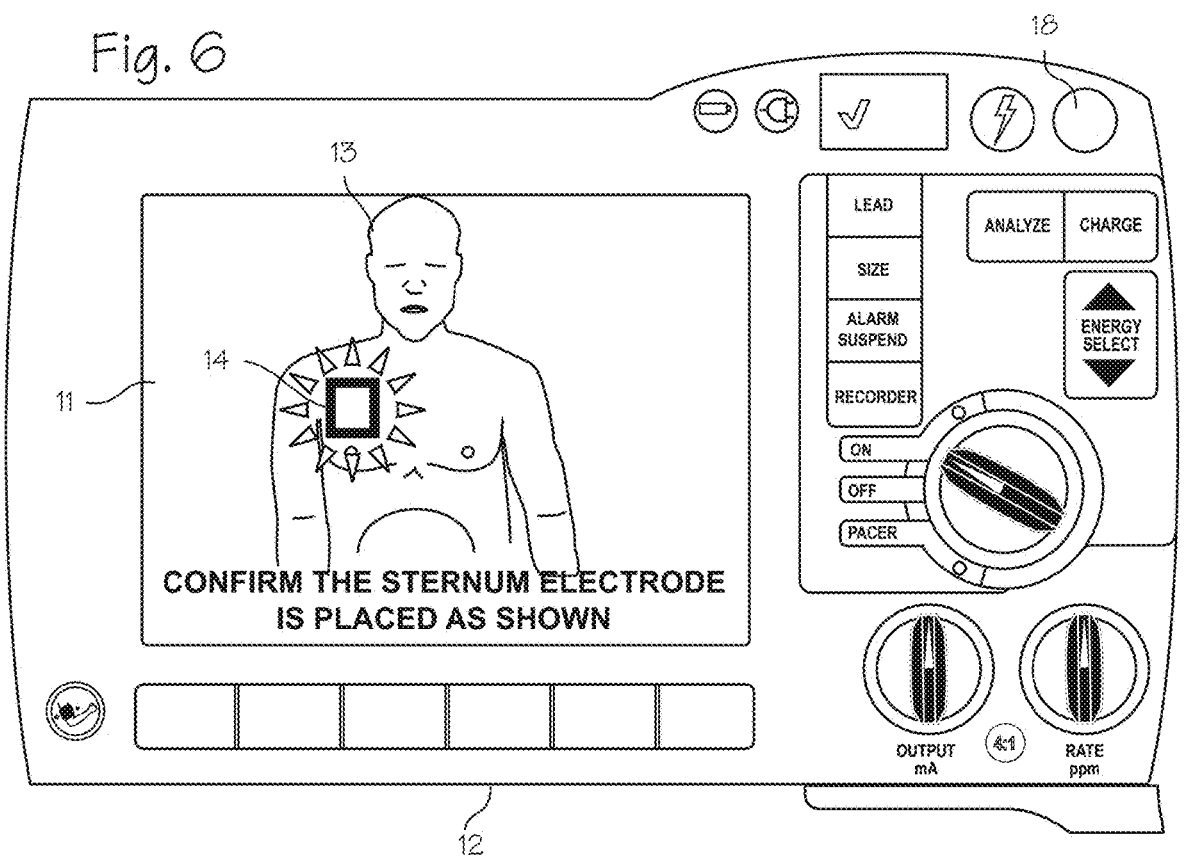

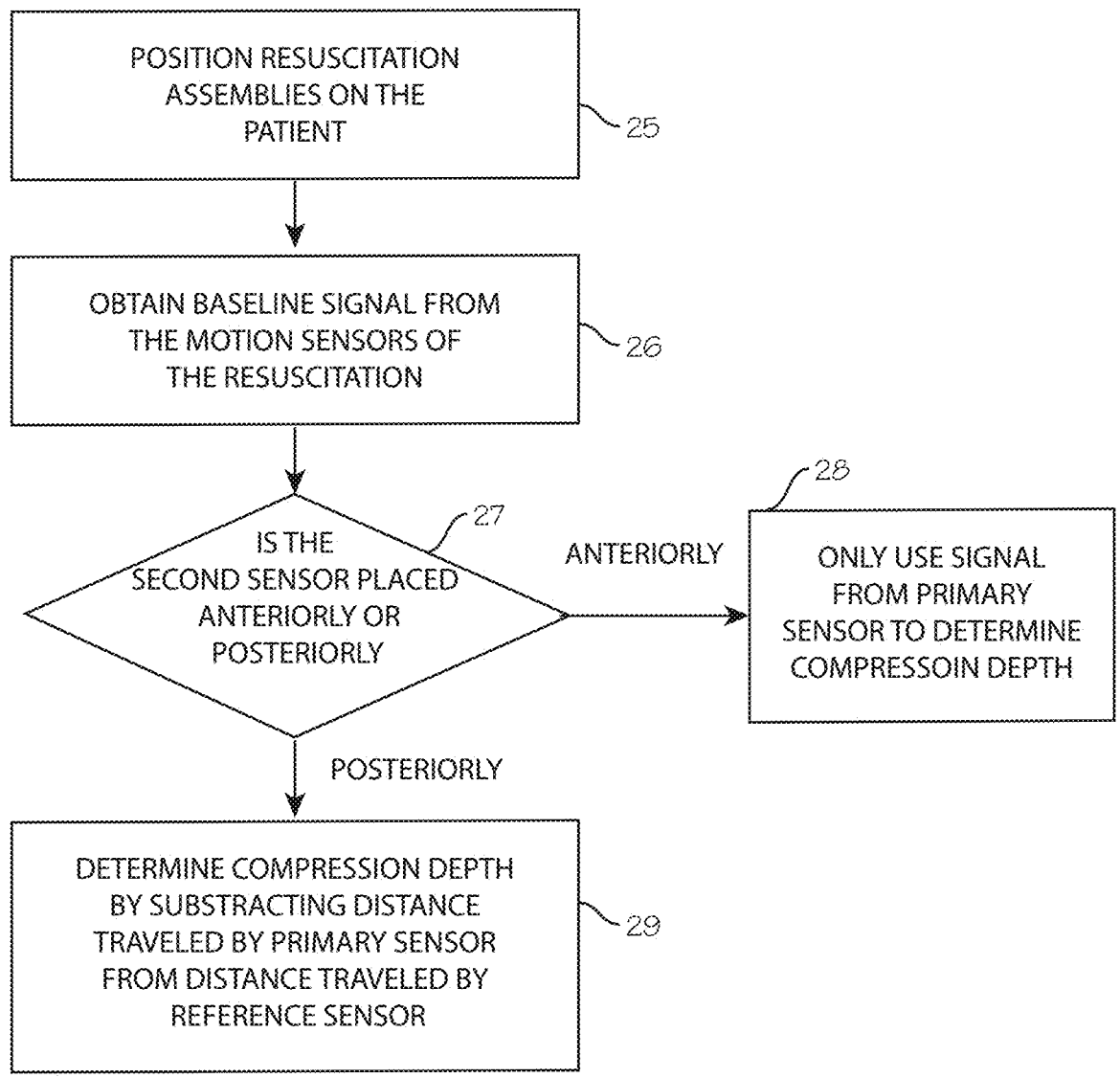

ECG AND DEFIBRILLATOR ELECTRODE DETECTION AND TRACKING SYSTEM AND METHOD

FIELD

The methods and devices described below relate to the field of resuscitation therapy.

BACKGROUND

Defibrillators are used to treat Sudden Cardiac Arrest with electrodes placed on the chest of the patient, and apply defibrillating shock to the heart of a cardiac arrest patient. The ECG of a cardiac arrest patient, properly measured and analyzed, indicates whether the patient's heart is exhibiting a shockable rhythm or a non-shockable rhythm. A shockable rhythm refers to an aberrant ECG which is subject to defibrillation, and restoration of a normal heartbeat, while a non-shockable rhythm refers to a normal ECG which needs no defibrillation, and to an aberrant ECG which is not subject to defibrillation. Ventricular fibrillation, for example, is a shockable rhythm, while pulseless electrical activity is an example of a non-shockable rhythm. Defibrillators are also capable of treating other dysrhythmias (irregular heartbeats), such as atrial fibrillation, bradycardia and tachycardia. The ECG of a patient can also indicate these conditions, and the defibrillator can be operated to apply cardioverting shock to the heart of patient experiencing dysrhythmias.

ECG diagnosis and delivery of shock can be accomplished with a ECG and a manual defibrillator, in which case a rescuer using the defibrillator analyzes the ECG to determine if the patient's ECG is shockable, and if so, apply the appropriate defibrillating shock to the patient. ECG diagnosis and delivery of shock can be accomplished with an Automatic External Defibrillator (AED), which is operable to automatically analyze the ECG to determine if the patient's ECG is shockable, and, if so, automatically apply the appropriate defibrillating shock to the patient (or advise an operator to operate the AED to apply the shock, in which case the devise may be referred to as a Semi-Automatic Defibrillator (SAD)). In each, the ECG is obtained through electrodes placed on the chest of the patient, and the defibrillating or cardioverting shock is applied through the same electrodes. For diagnosis and treatment of sudden cardiac arrest, the defibrillator uses two electrodes, with an apex electrode placed on the lower left front surface of the patient's chest, and the sternum electrode placed on the upper right front surface of the patient's chest. In diagnostic ECG monitoring systems, which are used to diagnose heart conditions in a patient not suffering from sudden cardiac arrest, many electrodes may be used to sense the ECG, and these electrodes are not useful for applying defibrillating or cardioverting shock.

The electrodes used with defibrillators are placed on the patient's body in clearly defined locations. A common arrangement for AED's is the anterior-apex scheme, described above, with an apex electrode disposed on the lower left front/medial surface of the patient's chest, just below and to the left of the pectoral muscle, and the sternum electrode (also referred to as the anterior electrode) placed on the upper right front surface of the patient's chest, below the right clavicle. For pacing, the preferred arrangement is the anterior-posterior scheme, which uses an anterior electrode disposed on the front left side of the chest, over the left precordium (that is, over the heart), and a posterior electrode disposed on the back of the patient, on the left side, beneath the heart and between the scapula and the spine at heart level. Diagnostic ECG systems use several small electrodes (up to fifteen electrodes in some systems) and electrode placement for these multi-lead systems is more complex.

Typical defibrillators use pre-packaged, multi-function, self-adhesive defibrillation (SAD) electrodes that both provide the functions of sensing the microvolt level activity of the heart's ECG signal as well as provide the conductive interface to the skin for delivering the therapeutic electrical shock. These self-adhesive defibrillation electrodes are typically much larger than standard commercial ECG electrodes used for diagnostic ECG: diagnostic ECG electrodes might have an active surface area of several square centimeters while self-adhesive defibrillation electrodes have a surface area of approximately 100 $cm^2$. Defibrillation electrodes are also capable of handling current levels that are at least several orders of magnitude greater than diagnostic ECG electrodes.

In diagnosing and treating a sudden cardiac arrest patient, proper placement of the electrodes is critical to obtaining a correct ECG from the patient which can be used to determine whether the ECG indicates a shockable rhythm. In diagnosing a patient with chronic heart condition, proper placement of the electrodes is critical to obtaining a correct ECG from the patient which can be used to diagnose various heart conditions. Improper placement causes changes in the ECG obtained through the electrodes. These changes can result in an ECG trace with artifacts such that the trace cannot be analyzed, does not reveal a shockable rhythm, or incorrectly indicates a shockable rhythm. When attempting to diagnose a cardiac arrest patient, an unusable ECG may result in failure to treat the patient, or delay in treating the patient, and loss of the opportunity to revive the patient. In the diagnostic ECG, misplaced leads can lead to artifacts which simulate clinical pathology (ectopic atrial rhythm, ischemia, or infarction) that does not actually exist in the patient, and this can lead to unnecessary treatments and even unnecessary invasive procedures. The artifacts may or may not be detectable even by clinical experts. Also, proper placement of the electrodes is important to delivering the proper amount of defibrillating or cardioverting energy to a patient. Thus, in each case, a technician must carefully place the electrodes in predetermined locations on the patient's body.

Although ECG electrodes provided for use with AED's are often packaged with very clear directions for placement, electrode misplacement is still an occasional problem with serious, perhaps fatal consequences.

SUMMARY

The devices and methods described below provide for identification of ECG electrodes being handled by a rescuer, followed by prompts indicating which electrode the rescuer has in hand and prompts indicating proper placement of that electrode. To detect the electrode being manipulated by the rescuer, motion sensors (accelerometers or other sensors) are mounted on the electrodes. (The system already knows which electrode is which, because each electrode is connected to a conductor cable which in turn is connected to a connector with unique inputs for each electrode). The system of the defibrillator to which the electrodes are connected is programmed (in addition to its programming for displaying and analyzing an ECG signal obtained through the electrodes, and generating and delivery defibrillating shock to the electrodes or separate paddles), to analyze the sensor input to determine a characteristic of the motion of the electrodes, determine which electrode is being handled, and prompt the rescuer to put the electrode on the patient in its proper position. The prompts may be verbal prompts or images displayed on a display screen of the defibrillator.

Devices and methods described below also provide for motion tracking of electrodes, in order to determine the location and orientation of ECG electrodes during handling and after placement, combined with analysis of the location and orientation of the electrodes to determine location of the electrodes relative to each other. To detect the relative location of the electrodes, a tracking system, such as in motion tracking or inertial navigation systems comprising accelerometers and/or other sensors, is mounted on the electrodes. The system of the defibrillator to which the electrodes are connected is programmed (in addition to its programming for displaying and analyzing an ECG signal obtained through the electrodes, and generating and delivery defibrillating shock to the electrodes or separate paddles), to analyze the sensor input to determine a the motion of the electrodes, track the movement, and determine the relative location and/or orientation of the electrodes, determine whether the relative location and/or orientation deviates from pre-determined acceptable values, and prompt the rescuer if the relative location and/or orientation does deviate from pre-determined acceptable values. The prompts may be verbal prompts, non-verbal prompts, audible prompts, text prompts and/or images (e.g., static, moving) provided by an appropriate component (e.g., display screen, speaker, etc.) of the defibrillator. The prompts may be feedback prompts where information is provided to the system and, based on an appropriate analysis, a prompt is issued to provide guidance to a user giving resuscitative treatment. Feedback may also involve one or more signals generated based on an analysis of information provided to the system, for issuing a prompt, controlling one or more components of the system, etc.

The sensor can be an accelerometer which generates an acceleration signal when it is moved. With an accelerometer on each electrode, the system can be programmed to analyze acceleration signals from the accelerometers to determine which is being handled by the rescuer, based on the difference between the acceleration signals from each accelerometer. The distinction can be made on the basis of the amplitude of acceleration or velocity (determined from the acceleration signals), under the assumption that the electrode in hand is subject to higher acceleration and/or velocity than the electrodes not being handled. Other motion sensors, including velocity sensors, magnetic sensors, and impedance can be used to detect motion and generate motion signals for use by the control system.

Though this new system will be described with emphasis on the typical two-electrode AED system which uses two detached electrodes, the system can be used in multi-function defibrillator systems and ECG diagnostic systems which use more electrodes.

In an illustrative embodiment, a resuscitation system for aiding a user in providing g resuscitative treatment to a patient is provided. The system may include a first electrode with a first motion sensor assembly disposed in fixed relation to the first electrode. The system may further include a second electrode with a second motion sensor assembly disposed in fixed relation the second electrode. The system may also include at least one processor, with memory, power supply and other processing components, where the at least one processor is configured to analyze motion signals from the first and second motion sensor assemblies to determine the location and orientation of the first and second electrodes relative to each other.

In various embodiments, the system may include a communication component configured to provide at least one prompt based on the analyzed motion signals to assist the user in providing the resuscitative treatment to the patient.

In certain embodiments, the at least one prompt from the communication component may include guidance for assisting the user in placement of at least one of the first electrode and the second electrode on the body of the patient. The at least one prompt may include one or more images of a patient indicating a preferred location for the user to place at least one of the first electrode and the second electrode on the body of the patient. The at least one prompt may include one or more images indicating the determined location of the first and second electrodes relative to each other. The at least one prompt may include at least one of a visual display, an image, a moving image, visual instructions, visual text, verbal audible instructions and non-verbal audible instructions.

In some embodiments, the at least one prompt from the communication component may include guidance for assisting the user in confirming placement of at least one of the first electrode and the second electrode on the body of the patient. The at least one processor may be configured to detect whether placement of at least one of the first electrode and the second electrode on the body of the patient has been confirmed based on the analyzed motion signals. In some embodiments, confirmation of placement of at least one of the first electrode and the second electrode involves detection of a manipulation by the user of the respective electrode.

In certain embodiments, the at least one processor is configured to estimate a size of the patient based on the determined location and orientation of the first and second electrodes relative to each other. The at least one processor may be configured to provide a chest compression signal based on the estimated size of the patient for providing chest compressions to the patient. The chest compression signal may result in a prompt (e.g., via a communication component) for providing guidance to the user relating to administration of at least one a preferred chest compression depth and a preferred chest compression rate. The at least one processor may be configured to provide a defibrillation energy signal based on the estimated size of the patient for administering a level of defibrillation energy to the patient. The at least one processor may be configured to provide a ventilation signal based on the estimated size of the patient for providing ventilations to the patient. The ventilation signal may result in a prompt (e.g., via a communication component) for providing guidance to the user relating to administration of at least one of a preferred ventilation tidal volume and a preferred ventilation minute volume.

In some embodiments, the at least one processor may be configured to analyze motion signals by comparing differences between at least one of acceleration and velocity signals from the first and second motion sensor assemblies. The at least one processor may be configured to determine whether the first and second motion sensor assemblies are packaged together, removed from the package and moving, or removed from the package and stationary. Upon a determination that the first and second motion sensor assemblies are packaged together or removed from the package and stationary, the at least one processor may be configured to calibrate measurements of the acceleration or velocity to estimate and compensate for at least one of RMS noise, offset and drift.

In some embodiments, the system may include a defibrillator operable to deliver shock to a patient through the first and second electrodes, where the at least one processor, with memory, power supply and other processing components and the communication component are part of the defibrillator. In some embodiments, the at least one processor, with memory, power supply and other processing components are part of the defibrillator and the communication component is part of a device (e.g., mobile device, tablet, personal digital assistant, cell phone, etc.) separate from the defibrillator.

In another illustrative embodiment, a resuscitation system for aiding a user in providing resuscitative treatment to a patient is provided. The system may include a first electrode with a first motion sensor disposed in fixed relation to the first electrode. The system may further include a communication component operable to issue placement prompts to the user. The system may include at least one processor, with memory, power supply and other processing components. The at least one processor may be configured to analyze motion signals from the first motion sensor to determine that the first electrode is moving, and may be configured to operate the communication component to provide at least one prompt based on the analyzed motion signals to assist the user in providing the resuscitative treatment to the patient.

In certain embodiments, the at least one prompt may be provided to assist the user in placing the first electrode on a first position of the body of the patient. The at least one prompt may include an image of a patient indicating a preferred location for the user to place the first electrode on the first position of the body of the patient.

In some embodiments, the system may include a second electrode with a second motion sensor disposed in fixed relation to the second electrode. The at least one processor may be configured to analyze motion signals from the second motion sensor to determine that the second electrode is moving, and may be configured to operate the communication component to provide at least one prompt based on the analyzed motion signals to assist the user in providing the resuscitative treatment to the patient. The at least one prompt may be provided to assist the user in placing the second electrode on a second position of the body of the patient. The at least one prompt may include an image of a patient indicating a preferred location for the user to place the second electrode on the second position of the body of the patient.

In some embodiments, the at least one processor may be configured to prompt the user to generate motion in the first electrode, and sense subsequent motion of the electrode, and thereby determine that the user is generating motion in the first electrode. The at least one processor may be configured to prompt the user to generate motion in the first electrode, and sense subsequent motion of the electrode, and determine that the motion signals from the second motion sensor indicate that the second electrode is stationary, and thereby determine that the user is generating motion in the first electrode.

In certain embodiments, the at least one prompt may include guidance for assisting the user in confirming placement of the first electrode on the body of the patient. The at least one processor may be configured to detect whether placement of the first electrode on the body of the patient has been confirmed based on the analyzed motion signals. Confirmation of placement of the first electrode may involve detection of a manipulation by the user of the first electrode.

BRIEF DESCRIPTION OF THE DRAWINGS

FIGS. 3 through 12 illustrate the defibrillator system and the various prompts that may be generated by the system.

FIG. 21 is a flow chart illustrating this method of controlling the method of compression depth calculation based on determined electrode placement.

DETAILED DESCRIPTION

Ventricular fibrillation (VF) is the most frequent initial rhythm in a witnessed sudden cardiac arrest and electrical defibrillation is the only effective treatment. Success of defibrillation is dependent on delivering sufficient transmyocardial current to depolarize a critical mass of myocardium, estimated to be approximately 72-80% of the ventricular mass. Factors affecting the transmyocardial current include transthoracic impedance, energy level and the ratio of current passing through cardiac tissue to current passing through non-cardiac tissues. This ratio can be increased by optimizing the position of the defibrillation electrodes. The current flow caused by defibrillation shock is mainly adopted by non-cardiac tissue. Unfortunately, it has been shown by researchers that even trained clinicians do a poor job of properly placing SAD electrodes, such as one study by Nurmi, et al., *Adherence To Guidelines When Positioning The Defibrillation Electrodes*, 61 Resuscitation 143 (May 2004) which found that only one in four medical professionals trained to defibrillate were able to place the defibrillation electrodes in the correct location.

Although SAD electrodes provided for use with defibrillators are often packaged with very clear directions for placement, electrode misplacement is a very serious problem, even with highly trained rescuers, with potentially fatal consequences to the patient. It would thus be desirable to have both manual defibrillators and AEDs provide automated, guided and interactive feedback to the user on the placement of electrodes, where the device is able to determine the location of the electrode, resulting in improved accuracy of SAD electrode placement, and ultimately improved defibrillation efficacy and higher survival rates.

Figure 1:
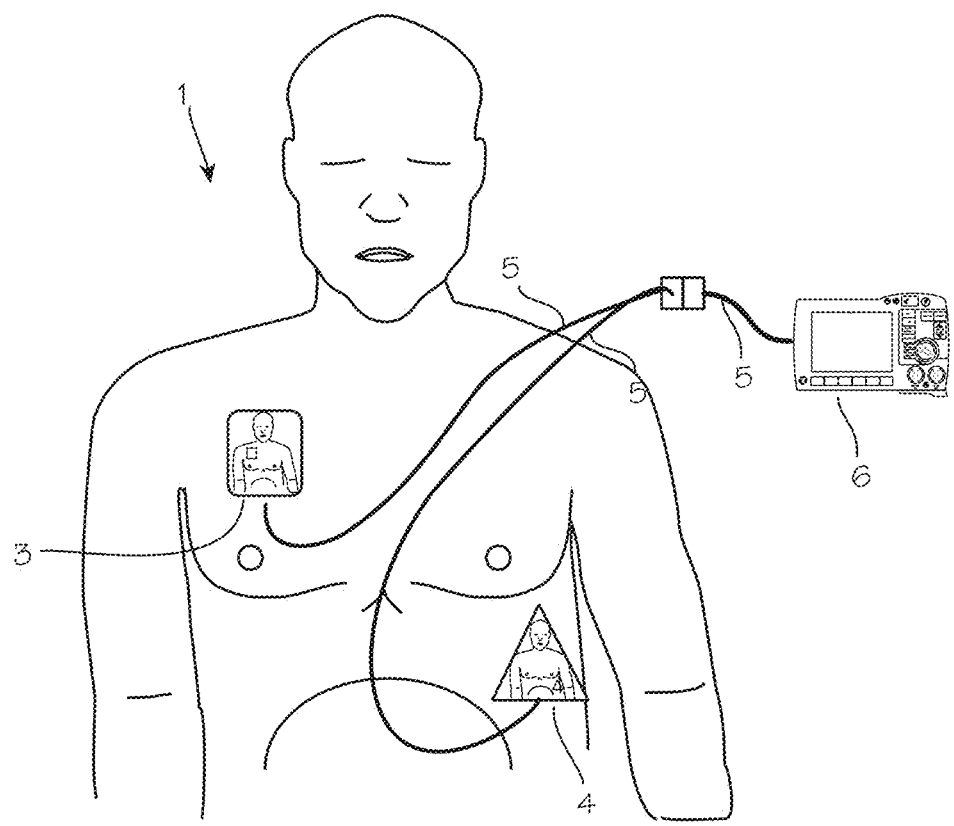
FIG. 1 illustrates placement of defibrillator electrodes on a cardiac arrest victim.

FIG. 1 illustrates typical placement of defibrillator electrodes on a cardiac arrest victim. The patient 1 is shown with two electrodes of an automatic emergency defibrillator or AED secured to the chest. The resuscitation system 2 depicted in FIG. 1 includes a ZOLL Medical R Series Monitor Defibrillator, which can operate as an AED, a semi-automatic defibrillator (SAD) or a manual defibrillator with a monitor, and can also be used for cardioverting and pacing. The sternal electrode 3 is shown in its proper position, on the anterior chest wall, on the right side of the chest between the armpit and the sternum, and just below the clavicle of the patient. The apex electrode 4 is shown in its proper position, on the anterior chest wall on the left side of the chest over the lower ribs, lateral to the sternum, at approximately the same level as the sternal notch, and to the left of the nipple with the center of the electrode in the mid-axillary line. The electrodes are connected through cables 5 to a defibrillator system which includes an ECG monitor and display for analyzing the ECG signals obtained through the electrodes and displaying the ECG waveform to a user, and a defibrillator operable to generate defibrillating shock and deliver that shock to the patient through the electrodes.

As discussed above, proper placement of the electrodes is necessary and although various ergonomic tactics are used to avoid confusion, including providing electrodes of differing shapes and colors, or with pictograms, diagram or schematic instructions printed on the electrodes, improper placement is a common mistake that renders the defibrillator inoperable. The ECG analysis function of the monitor portion of the defibrillator may not be able to diagnose the condition of the patient if the electrodes are switched, and the defibrillator may deliver inappropriate levels of therapeutic shock if the electrodes are too far from the correct locations.

Figure 2:
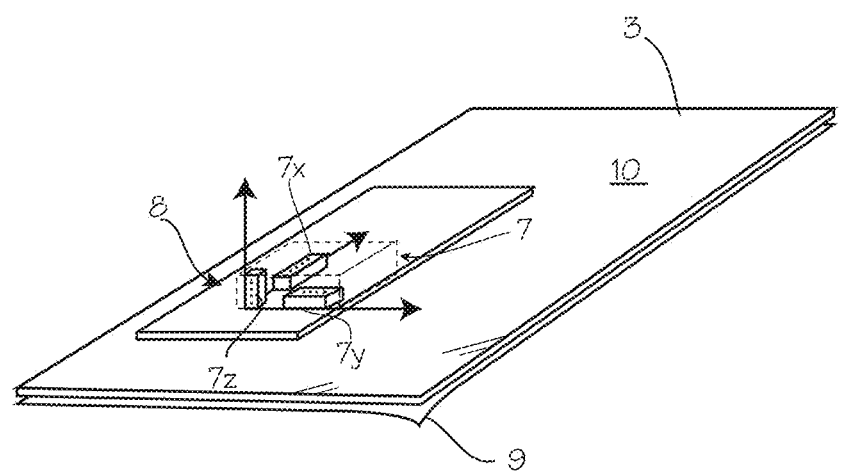
FIG. 2 illustrates an ECG electrode with an accelerometer assembly.

To address the first of these problems (the electrodes are switched), a sensor is secured to one or both of the electrodes and operably connected to the defibrillator system to provide motion signals to the defibrillator system. The sensor may be incorporated into the electrode, fixed to the electrode, fixed to the cable immediately adjacent to the electrode, or secured in any other which ensures that the sensor moves in tandem with the electrode and/or is disposed in fixed relationship to the electrode such that movement of the electrode results in corresponding movement of the sensor. Assuming that the electrodes are connected to the defibrillator (which may be assured in systems where the electrodes are hard-wired to the defibrillator, or confirmed by sensing the connection to the defibrillator), the control system receives motion sensor signals, and correlates the motion sensor signals from each electrode to the electrode on which it is mounted, and determines a motion characteristic of each electrode which indicates whether the rescuer is handling and moving an electrode, and then generates a prompt indicating the proper placement of the electrode. FIG. 2 illustrates one of the electrodes, which may be the apex or sternum electrode, fitted with a motion sensor 7. In this illustration, the motion sensor is a multi-axis accelerometer assembly 8 with three distinct accelerometers $7x$, $7y$ and $7z$ arranged orthogonally to each other, capable of detecting acceleration on three orthogonal axes. A single sensor accelerometer, such as the Analog Devices ADXL335, which employs a single sensor such as a capacitive plate device, referred to as an accelerometer, to detect acceleration on multiple axes, may be used in place of the accelerometer assembly, and single or double axis accelerometer assemblies may also be used, and two or three single or double accelerometer assemblies may be combined into an accelerometer assembly to detect acceleration on three axes. Other motion sensors may be used. In certain embodiments, multi-axis accelerometers, e.g. three-axis accelerometers, may be able to provide signals that further determine relative orientation of the respective electrode assemblies by measuring parameters indicative of motion along each axis. The motion sensor may also include a gyroscope for determining orientation of the sensor (and, in some cases, the electrode assembly) by way of tilt or rotation. Generally speaking, while an accelerometer senses acceleration or gravity, motion or displacement of the accelerometer can be determined through a series of calculations (e.g., double integration, etc.). Accordingly, it can be determined whether electrode placement occurs on the anterior, posterior and/or the lateral side of the patient. The electrode has a skin contacting surface covered with a conductive material, and this surface may be covered with an impedance matching gel and protected by a peel-away backing 9. The front surface 10 of the electrode may be imprinted with indicia, such as the patient icons shown in FIG. 1, to illustrate the proper placement of each electrode.

The defibrillator and its associated display are depicted in FIGS. 3 through 12. The control system operates to provide visual output in a portion of display 11 to provide feedback and/or provide prompts to the rescuer. The display is provided in the front panel of an AED box 12, such as ZOLL's R Series automatic external defibrillator. The AED can accomplish various functions, including ECG monitoring, defibrillation, pacing, and monitoring of other parameters. When used for placement prompting, the display includes an icon 13 of the CPR victims, icon 14 representing the sternum electrode, and icon 15 representing the apex electrode, a display area 16 for displays 17 of visual prompts, and a speaker 18 for providing audio prompts. The user communication component, which may include a display, speaker and/or any other component suitable for providing prompts, provide means for issuing prompts to the rescuer.

When a rescuer sets up the defibrillator for use on a cardiac arrest victim the rescuer must turn on the defibrillator and apply the electrodes onto the patient. This may be done in any order, and currently our user manuals direct the rescuer to apply the electrodes to the patient before turning the defibrillator on (R Series Manual Rev. K, page 3-4), but the defibrillator is also operable to prompt the rescuer to apply and connect the electrode pads if the defibrillator does not detect connected electrodes and does not sense that the electrodes are disposed on the patient. The method presented herein can be used in either scenario, with some variation in the algorithm.

In the case where the defibrillator system is energized before the electrodes are placed on the patient, the system will, according to its programming, present a visual or audio prompt (or both) instructing the user to select an electrode. The system may prompt the rescuer to choose a specific electrode, or it may just prompt the rescuer to select an electrode, and also prompt the user to apply the electrode to the patient. The system will receive and interpret motion signals from the electrodes as the rescuer handles the electrodes, and determine which electrode is in hand, being handled by the rescuer, based on the motion signals. The system will then prompt to rescuer to inform the rescuer which electrode is in hand, and where it should be placed. Thereafter, the system will prompt the rescuer to apply the second electrode, and optionally may continue to receive and interpret motion signals from the electrodes, and determine which electrode is in hand and prompt the rescuer to inform the rescuer which electrode is in hand, and where it should be placed. In the two electrode system, monitoring of the second electrode can serve to confirm that the identification of the first electrode was correct, thus resolving any potential ambiguity.

Figure 3:
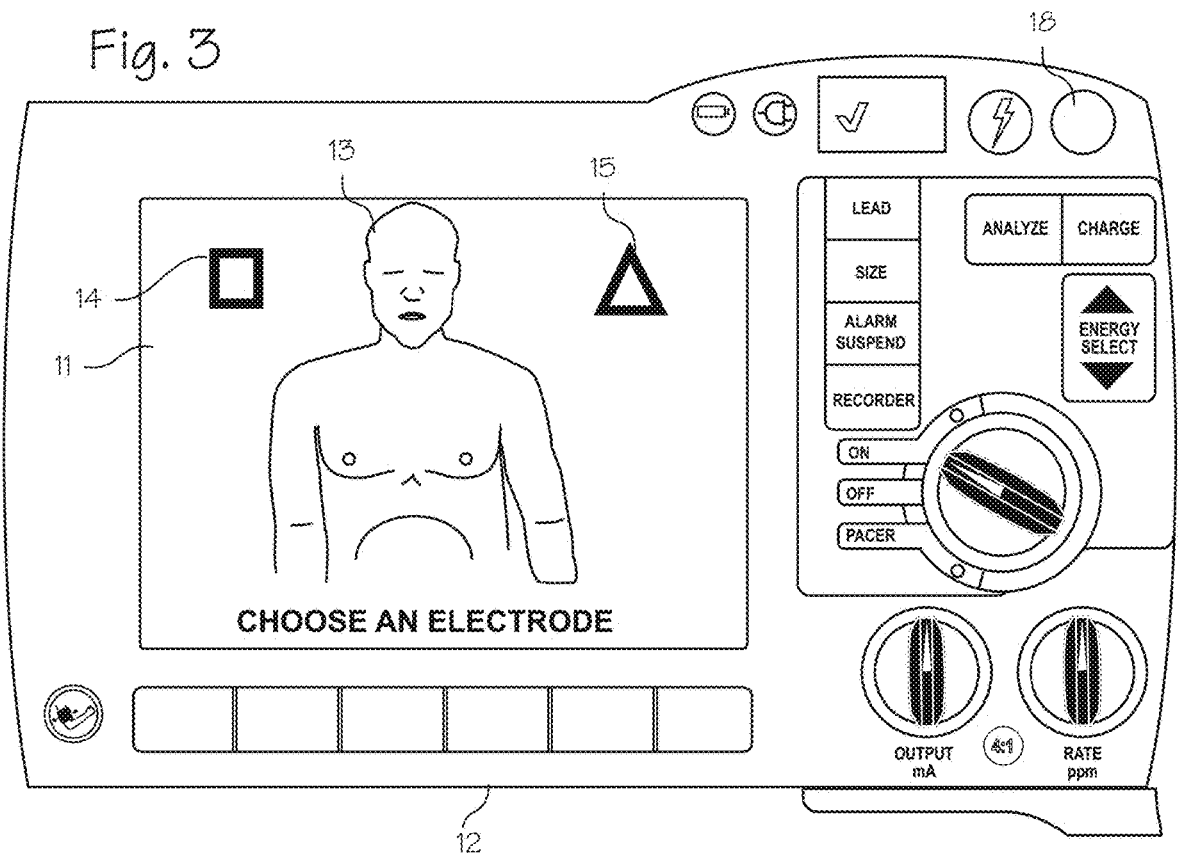
Figure 7:
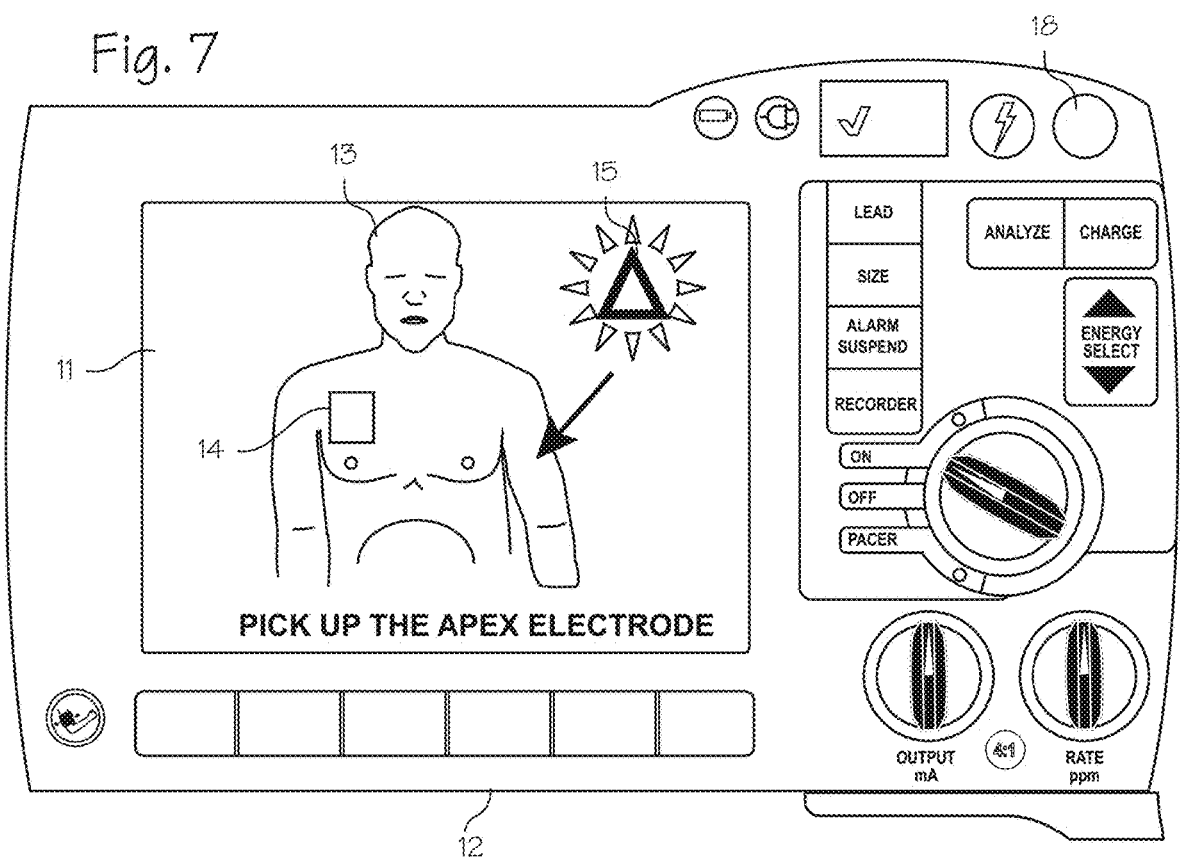
Figure 8:
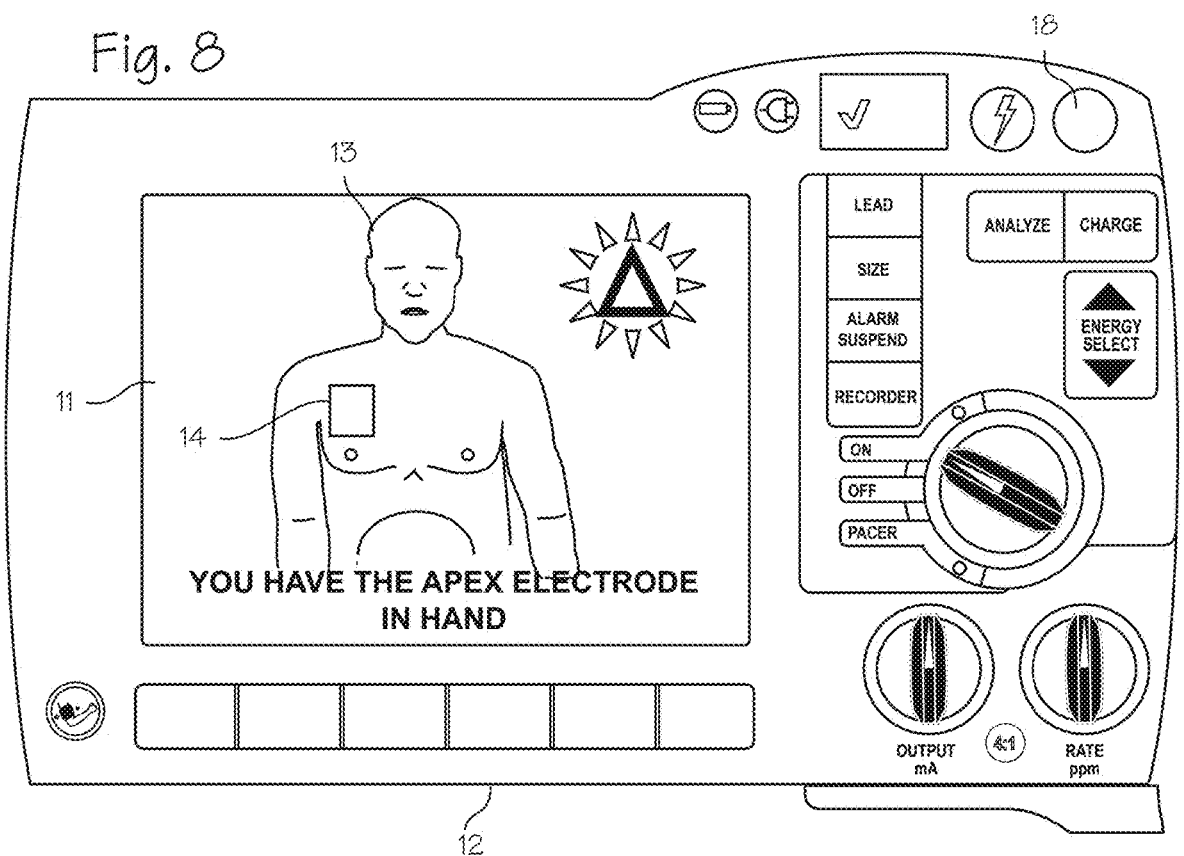
Figure 9:
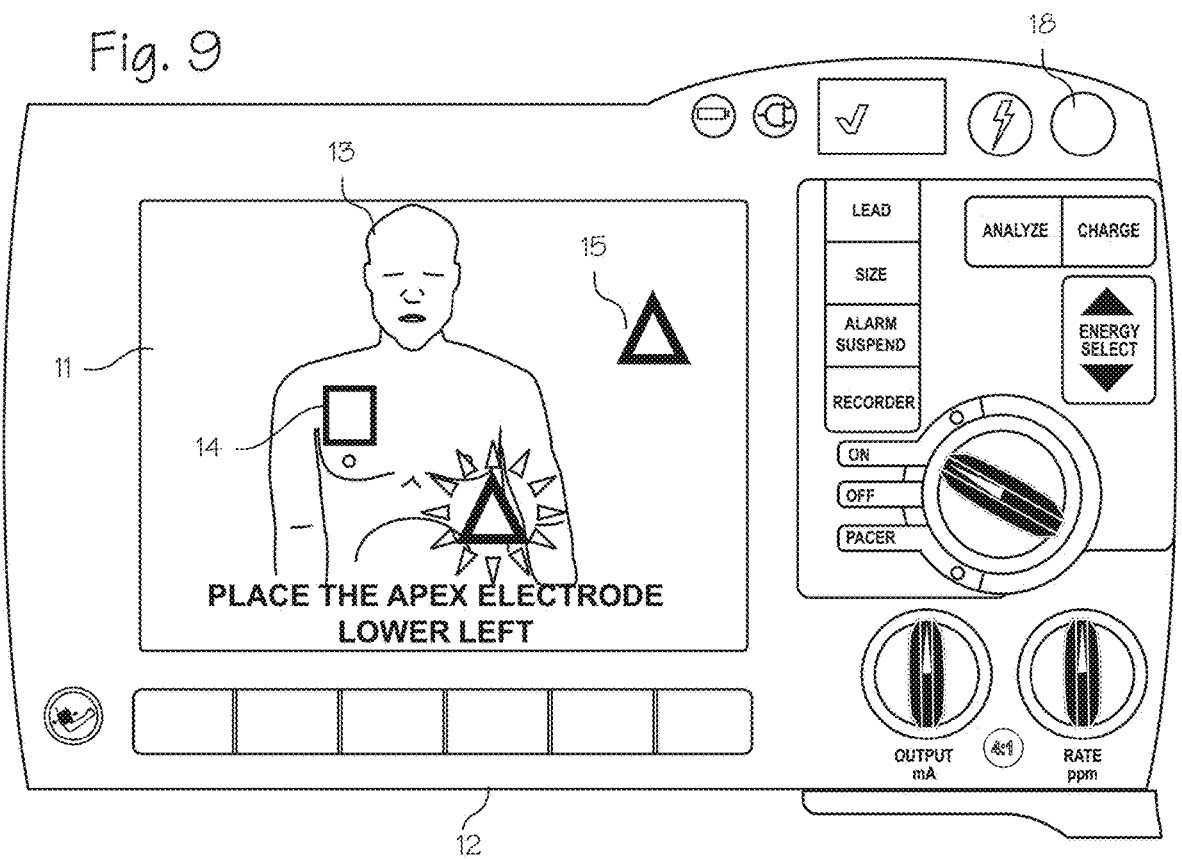
Figure 10:
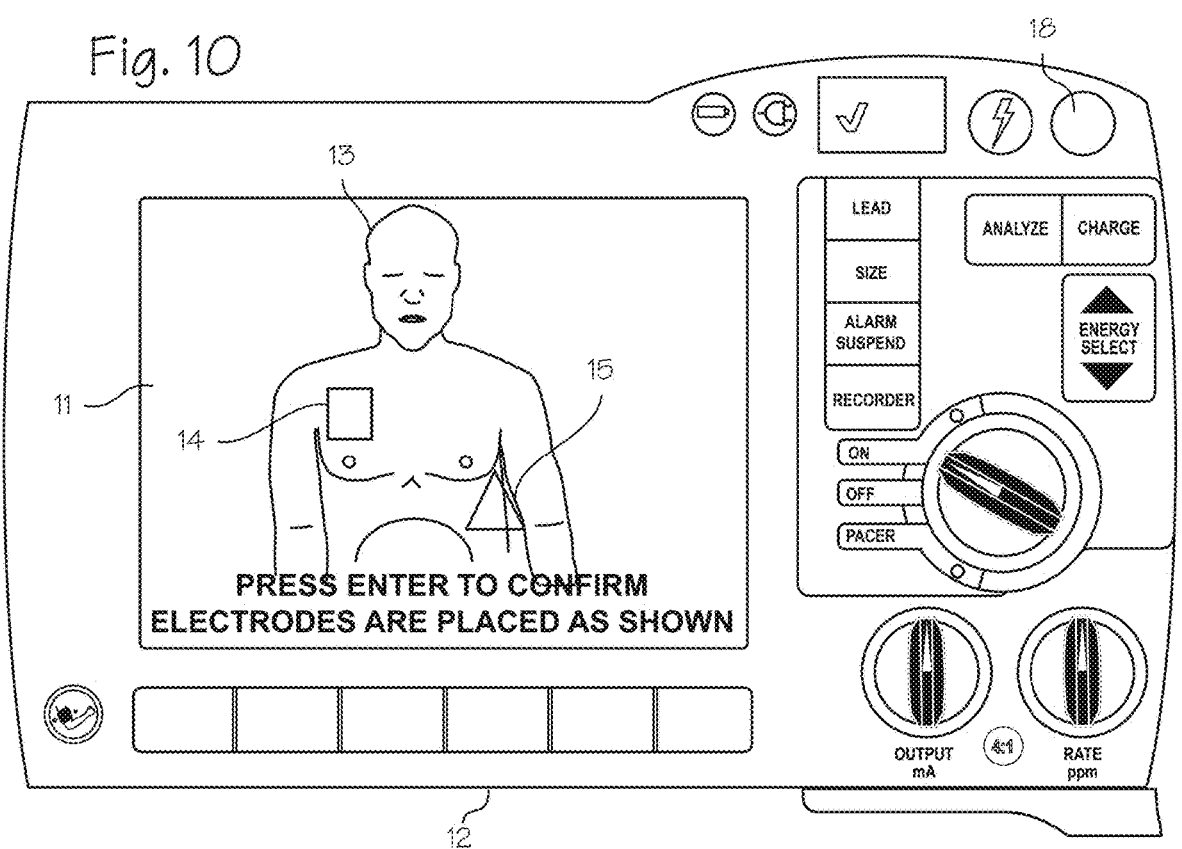
Figure 11:
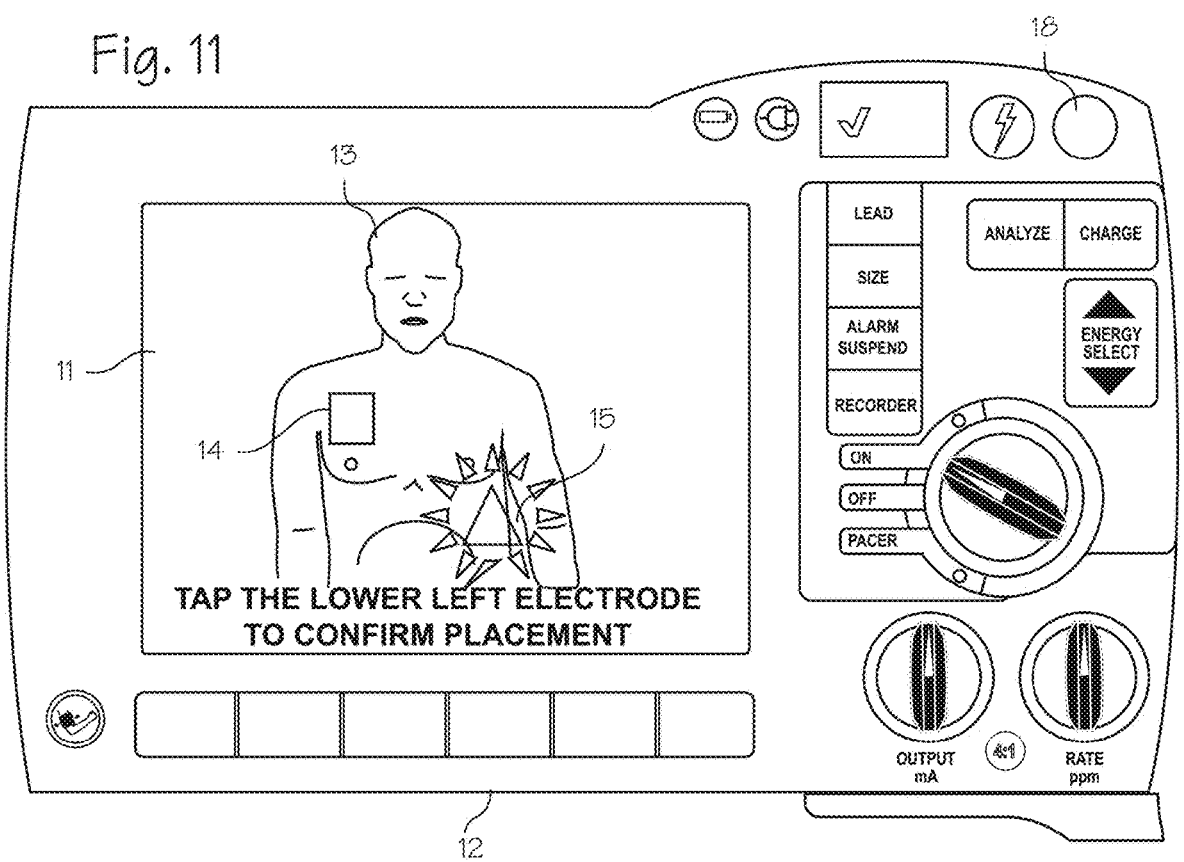
Figure 12:
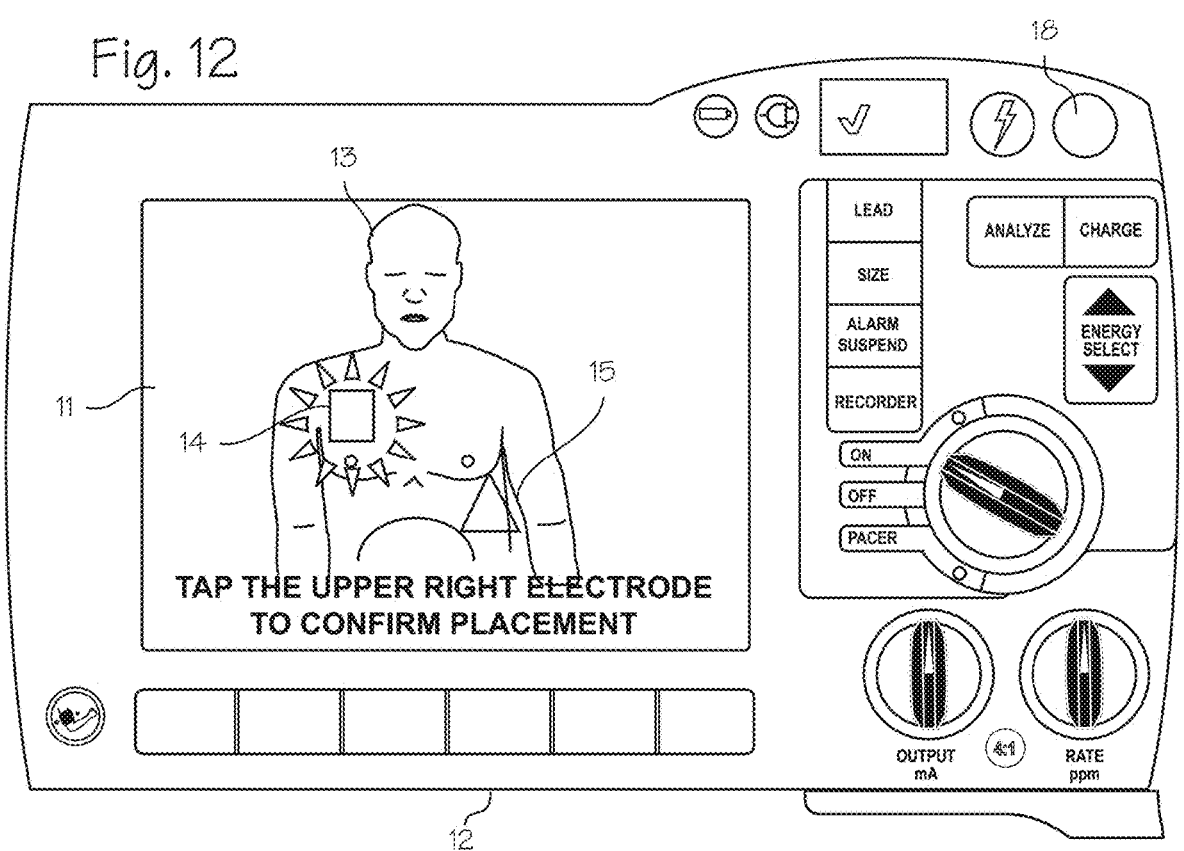

These steps are illustrated in FIGS. 3 through 12. FIGS. 3 through 12 illustrate the defibrillator system and the various prompts that may be generated by the system. In FIG. 3, and initial prompt, such as "Choose an Electrode" is presented. After this prompt, the system analyzes motion signals generated by the motion sensors to determine which electrode is in motion, thus indicating that it is being handled by the rescuer. In response to this determination, the system presents the information of FIG. 4, communicating to the rescuer that the sternum electrode is in hand and presents the prompt of FIG. 5 prompting the rescuer to "Place the Sternum Electrode Upper Right." FIG. 6 illustrates an optional step in which the system prompts the rescuer to confirm that that sternum electrode is properly placed. FIG. 7 prompts the rescuer to pick up the apex electrode, upon which the system monitors motion sensor signals from the apex electrode, and, upon sensing motion of the sternum electrode, the system presents the message of FIG. 8, confirming to the rescuer that the apex electrode is being handled. FIG. 9 illustrates a prompt which prompts the rescuer to place the apex electrode. FIG. 10 illustrates a prompt issued to prompt the rescuer to provide input to indicate that the electrodes are properly placed. Also, as shown in FIGS. 11 and 12, the system can generate prompts to instruct the rescuer to tap the electrodes corresponding to the icon, which will generate motion signals which can be analyzed by the system to confirm placement. The prompts issued by the system may be issued conditionally, meaning that the control system is programmed to issue prompts upon determining a condition which, according to its programming, leads to issuance of a prompt.

The textual visual prompts may be accompanied by a graphic visual prompt, as shown, with additional visual characteristics such as highlighting, pulsing, glowing, flashing or otherwise manipulating the screen icon of an electrode to make it more noticeable to a typical rescuer. Visual prompts can also include video, pictures, schematics and other graphical elements. The prompt may be an audio prompt generated by the control system and issued through a speaker, and the system can issue both audio prompts and visual prompts conveying the same messages.

Upon detection of motion signals from both electrodes, where the motion signals of one electrode are indicative of significant motion while at the same time motion signals of the other electrode are indicative of distinctly less motion than the motion of the first electrode, the system will interpret the more significant motion signal as indicative that the associated electrode is being manipulated by the rescuer, and issue prompts directing proper placement of that electrode.

The system can be implemented with a motion sensor on only one electrode, in which case handling of one electrode will result in generation of motion signals while handling of the other electrode will not result in generation of motion signals. In this system, when the first electrode is handled, the system will receive corresponding motion signals, and will not receive motion signals when the second electrode is handled. Thus, upon prompting the rescuer to choose and place an electrode, the system will monitor the motion sensor output, and determine based on the motion signals which electrode is being handled. The system may prompt the rescuer to provide input, through the interface, indicating that the user is handling an electrode. If the rescuer chooses the electrode with the sensor, handling will result in motion signals, and the system determines that the rescuer is handling the first electrode, and provides appropriate prompts for placement. If the rescuer selects the electrode without the sensor, handling (confirmed by input) will result in no motion signals, and the system determines that the rescuer is handling the second electrode, and provides appropriate prompts for placement.

To determine that an electrode is being manipulated by a rescuer, the system analyzed motion signals from the motion sensor on each electrode. The natural actions of the rescuer in picking up an electrode, peeling off the backing, in preparation for placing the electrode, results in generation of significant motion signals, while the relative quiescence and lack of motion of the electrode which is not being handled leads to generation of little or no motion signals. Thus, the system can determine that an electrode is being handled by analyzing motion signals and choosing the electrode associated with significant motion, exceeding a predetermined threshold. For example, motion indicative of acceleration exceeding a suitable threshold (for example, of 16 in/sec$^2$) an be taken as the necessary indication that an electrode is being manipulated, and is therefore the electrode subject to an earlier prompt to handle the electrode. Comparison of the motions signals from each electrode can also be used to determine that a particular electrode is in hand. For example, the system can interpret motion signals from a first electrode indicative of acceleration exceeding a certain threshold (for example, one or two in./sec$^2$), combined with motion signals indicative of acceleration below another threshold of only (for example, one in./sec$^2$), as an indication that the electrode subject to the higher acceleration is the electrode being handled. This can be combined with additional motion sensor information to aid in the determination, or confirm the determination. For example, the system can interpret motion signals indicative of motion along three axes in one electrode (indicative of being picked up, removed from packaging and unpeeled), combined with motion signals from the other electrode indicative of motion restricted to motion along only one or two axes (indicative of sliding on the ground next to the patient) as an indication that the more mobile electrode is in hand, being manipulated by the rescuer.

In cases where a rescuer energizes the defibrillator after placing the electrodes on the patient, it may make more sense to determine where each electrode is placed, and interpret the ECG obtained from the patient accordingly (assigning in software the designation of which electrode is the sternum electrode and which electrode is the apex electrode). Thus, if the defibrillator system senses that the electrodes are in place (by sensing the connector and detecting a typical impedance between the electrodes or from input from the rescuer), the system, operating according to its programming, will initiate the confirmation steps illustrated in FIGS. 11 and 12, prompting the user to tap or otherwise cause the motion sensor of one or both electrodes to generate a motion signal. Where the motion sensor is an accelerometer assembly, the motion signal generated by tapping the electrode, near the accelerometer sensor, will be characterized by rapid, short distance up and down, or back and forth, motion of sensor, or rapid accelerations and decelerations along a single axis of the sensor (also accompanies by very little movement of the other electrode), and this will be readily discernable by the control system. Thus, the system may interpret the ECG signal obtained from the electrodes based on the actual position of each electrode, rather than an assumed position.

To resolve ambiguity, the system can prompt the rescuer to shake or tap the electrode in hand, and interpret accelerations of one electrode that exceeds the other immediately after the prompt as an indication that the electrode experiencing acceleration higher than the other is the electrode in hand, and then issue placement prompts. The system can be programed to confirm correct placement of a first electrode, by monitoring the acceleration of a second electrode and detecting accelerations of second electrode which are higher than the first, previously placed electrode, which should be experiencing little or no acceleration because it is secured to the patient. If the motion of the electrodes differs from the expected motion, the system can issue prompts to shake or tap the second electrode to create unambiguously high acceleration compared to the in-place electrode, and issue appropriate placement prompts or issue prompts to prompt the rescuer to confirm that the electrode placement is correct.

Various levels of electrode motion can be used to resolve ambiguity. For example, electrode velocity exceeding an appropriate threshold (for example, 16 inches per second), especially when rapidly shifting directions, with motion on any axis shifting from positive to negative two or more times per second, is an example of movement that can unambiguously identify an electrode that is being shaken. The system can also combine this with motion sensor signals from the other electrode which are indicative of little or no motion to further confirm which electrode is being handled. Electrode acceleration exceeding an appropriate threshold (for example, 16 in/sec$^2$) can also be taken as an unambiguous indication that an electrode is being shaken. The control system can also combine this with motion sensor signals from the other electrode which are indicative of little or no acceleration to further confirm which electrode is being handled.

Figure 13:
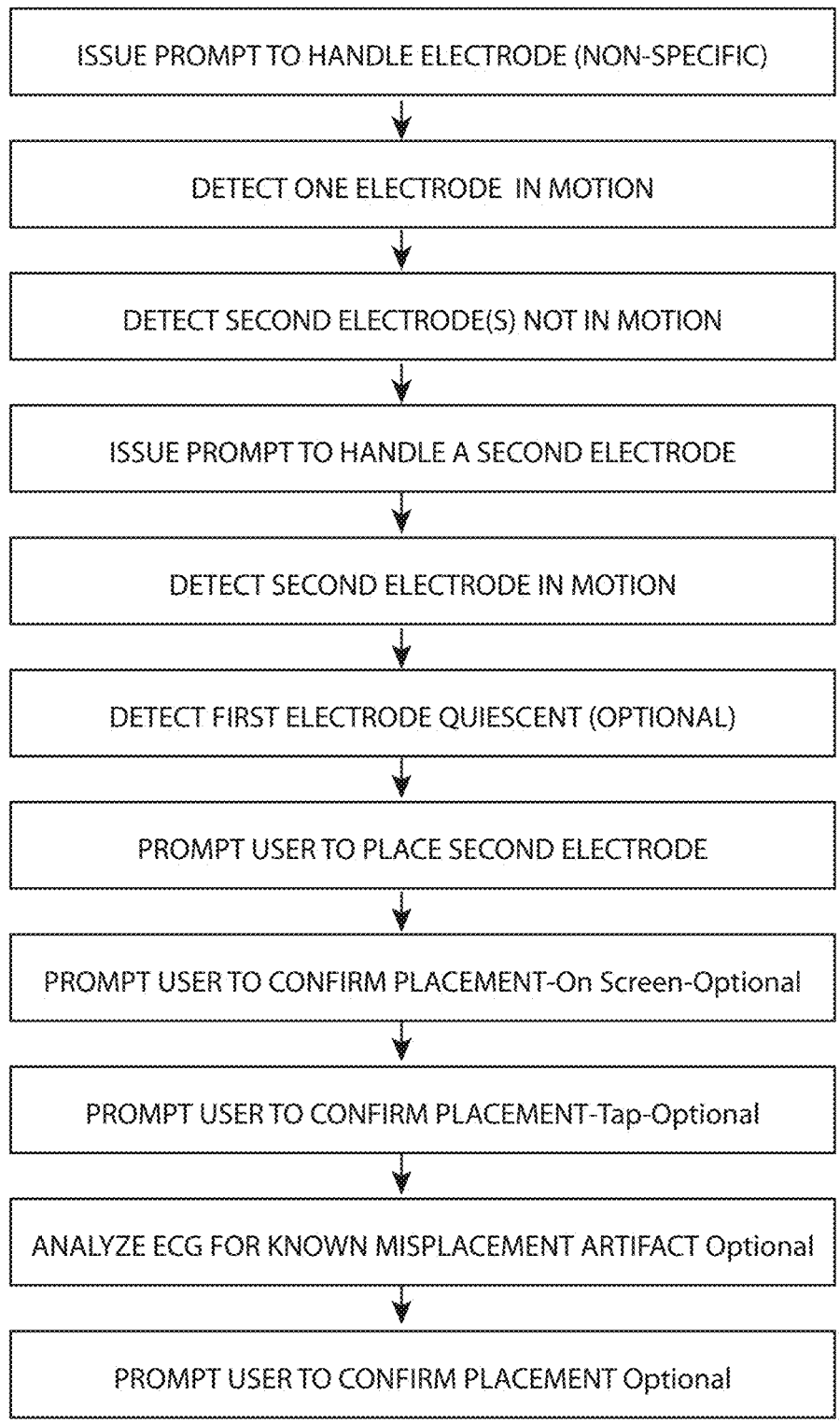
FIG. 13 is a flow chart illustrating an algorithm useful for implementing the method disclosed in FIGS. 3 through 12.

FIG. 13 is a flow chart illustrating an algorithm useful for implementing the method disclosed in FIGS. 3 through 12. As described above, some of the steps are optional, but are useful to confirm a determination made in an earlier step, or prompt confirmation in the form of input or a confirming action from the technician that a previous step has been completed. For example, if after the first prompt, one electrode exhibits motion that unambiguously indicates that it is being moved, the step of detecting that the other electrode is not in motion may not be necessary. If the system is implemented with only one motion sensor on one electrode, this step of course is not performed by the system. The step of analyzing the ECG for known misplacement artifacts may be used in electrode placement schemes in which misplacement artifacts are recognizable, and dispensed with in other systems.

In a more sophisticated electrode detection system, the system may be implemented to track the motion of the electrodes. Sensors on the electrodes, combined with programming of the control system to use motion-sensing data from the sensors to track the movement of the electrodes, can be operated to determine the location and orientation of the electrodes relative to each other (in addition to, or in lieu of, the method described in the preceding paragraphs). This can be accomplished by securing a motion tracking system, or sensing components of a motion tracking system, to the electrodes, and operating the control system to receive initial motion signals (or other inputs) to confirm that the electrodes are co-located, and thereafter tracking the motion of each electrode, and then detecting or accepting input indicating that the electrodes are in place on the patient, and, when placement on the patient is confirmed, analyzing the motion signals to determine the installed location, and thereafter prompting to indicate that the spacing between electrodes is within predetermined acceptable limits. The prompts can inform the user that the distance between the electrodes is within predetermined limits, or exceeds predetermined limits, or that the relative orientation of the electrodes is within predetermined limits, or exceeds predetermined limits. In addition to guiding and/or confirming location of the electrodes, the location information can be used by the system to estimate or determine the size the patient based on anthropometric models. Correspondingly, the system can control the defibrillator to adjust the energy applied to shock the patient depending the size of the patient. Or, as discussed further below, based on the estimated or determined size of the patient, the system may provide signals and/or prompts for adjusting other resuscitative therapies, such as chest compressions and/or ventilations.

The motion sensing system may include multi-axis accelerometers and a multi-axis gyroscopes (the ADIS16362 inertial system from Analog Devices, or the iNEMO® M1 motion sensing system manufactured by STMicroelectronics, which also includes a multi-axis magnetometer, are suitable). The necessary computations may be performed on a microprocessor in the motion system (as provided in the iNEMO® M1) or in the defibrillator. The microprocessor employs information from the sensors (including, for example, linear acceleration and/or gravity) to determine the location and orientation of the electrodes in a three-dimensional space.

Figure 14:
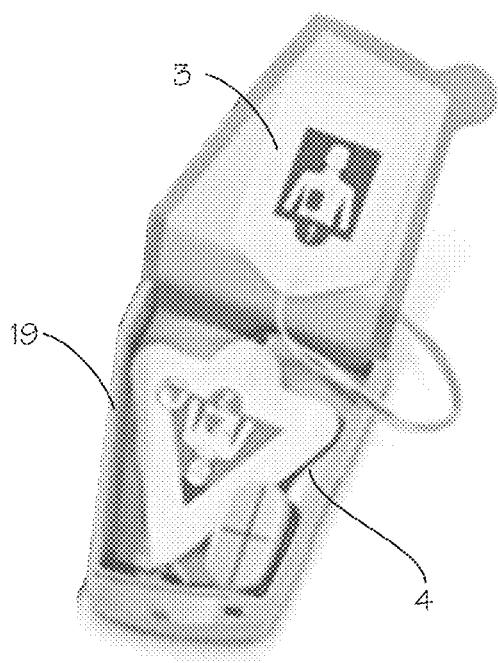
FIG. 14 illustrates an ECG electrode carry envelope.
Figure 15:
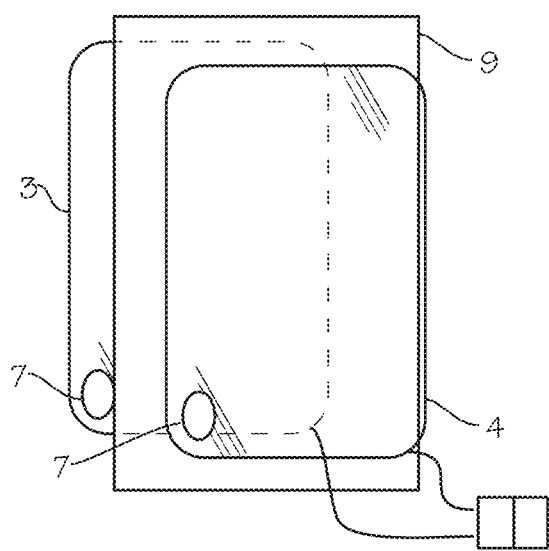
FIGS. 15 and 16 illustrate ECG electrodes disposed on a backing sheet, with sensors located at the same location on each electrode.
Figure 16:
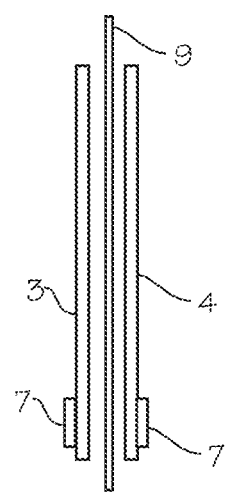

FIG. 14 illustrates a typical arrangement of multi-function electrodes 3 and 4 in a carry envelope 19, the electrodes may be disposed on the inner walls of the carry envelope. FIGS. 15 and 16 illustrate ECG electrodes 3 and 4 disposed on a backing sheet 9, with sensors located at the same location on each electrode. (The carry envelope provides sealing for the electrodes to keep them from drying out, as well as mechanical protection from bending and physical damage during transport. Typically, when the envelope is closed, there is an outer perimeter seal, providing humidity sealing.

Alternatively, the electrodes may be faced towards each other with the envelope closed and either disposed with their self-adhesive surfaces on a common, removable backing 9, as illustrated in FIGS. 15 and 16, or on separate, removable backings.) The electrodes, when stored, are thus typically located side-by-side, in facing relationship, such that motion sensors on each electrode can be assumed to be at the same point when the carry envelope is closed, for purposes of the motion tracking needed to determine their eventual relative position. Depending on the orientation of the sensors, when the electrodes are held together mechanically by the packaging, the electrodes and their associated motion sensors may see the same acceleration or movement along all sensed axes, or they may see the same acceleration and motion on axes parallel to the plane defined by the electrodes and acceleration and motion along the axis perpendicular to the plane defined by the electrodes. When the package is opened, in the case of FIG. 14, or when one or more of the electrodes 3 and 4 are removed from the backing 31 in the case of FIGS. 15 and 16, the acceleration, velocity or other measure of motion of the two electrodes as sensed by the sensors and determined by the system, based on the sensed signals will diverge significantly, and the start of this divergence of the two electrode motions can be interpreted as an origin point for the electrodes, and a starting point for tracking calculations.

The system may be programmed so that, as soon as the system is turned on, it begins tracking the orientation and trajectory of the motion sensors. If the two motions and orientations are consistent with co-location, the system takes this as indicating that the electrode package is closed in the case of FIG. 14, or that the electrodes are still attached to the backing, in the case of FIGS. 15 and 16. In some embodiments, as soon as the system detects that the relative spacing between the motion sensors exceeds a threshold, for instance of 0.2 to 0.5 inches, it is then known that the package (FIG. 14) is being opened or that the electrode is being removed from the backing (FIGS. 15 and 16).

Alternatively, the defibrillator may track the relative velocity or acceleration between the motion sensors to determine if the package is being opened or an electrode removed from the backing. For instance, if the motion sensor is a multi-axis motion sensor such as is described above, the output of each sensor at each sampling interval will be a three-component vector [$a_x$ $a_y$ $a_z$], where the three values are the linear acceleration components for the x, y, and z axes, respectively. A similar set of data will result for the rotational motion components. Thus, for any sample interval i, the relative acceleration, $\Delta A_i$, is:

$$\Delta A_i = [a_{xi1}\ a_{yi1}\ a_{zi1}] - [a_{xi2}\ a_{yi2}\ a_{zi2}]$$
$$= [(a_{xi1} - a_{xi2})(a_{yi1} - a_{yi2})(a_{zi2} - a_{zi2})],$$

where $a_{xi1}$, $a_{yi1}$, and $a_{zi1}$ refer to the i'th value of the first sensor, and $a_{xi2}$, $a_{yi2}$, and $a_{zi2}$ refer to the i'th value of the second sensor. Relative velocity components may be calculated by integrating the relative acceleration components.

Because the two sensors are mechanically coupled to each other via either the backing 9 or the envelope 19, any value of any component of $\Delta A_i$, or of the magnitude of $\Delta A_i$, that is greater than a threshold larger than the combined noise-floor and offsets of the two sensors, will determine whether the two sensors are separating from each other. For instance, the typical output noise specified for the ADIS16362 inertial system from Analog Devices is 5 mg rms. Assuming a Gaussian distribution and the two noise sources are independent, then the threshold of relative acceleration would be 20 to 25 mg. In other embodiments, the relative velocity might be used by itself, in a similar fashion, or used in conjunction with $\Delta A_i$ to augment the accuracy and timing of detection of the separation of the motion sensors from each other. Techniques may be used, known to those skilled in the art, such as zero-velocity updates (ZUPT) or Zero-Velocity Detection (ZVD), whereby a state machined is maintained that determines the two electrodes are still attached to each other, or having started separating. If the electrodes are determined to still be attached to each other, packaged together, then the processor will perform calibration of the sensors and the estimation of $\Delta A_i$. The processor may also perform calibration if the electrodes are determined to be removed from the package and stationary. The calibration intervals may be as frequently as every 1 millisecond or as infrequently as at intervals of 10 to 30 minutes, while the device is turned on. The intervals may be regular or irregular. For instance, the calibration may be based on a time interval when the state of the electrode spacing is determined to be that they are still attached to each other, or, when they are determined to have been in the process of separating, the calibration may occur upon zero velocity detection, using such algorithms as described by Skog, et al, *Zero-Velocity Detection—An Algorithm Evaluation*, 57 IEEE Trans. Biomed. Eng. 2657 (November 2010). The calibration may also be performed while the device is off, from the user's perspective, i.e. a "power-down" mode with no display and minimal power requirements, but is actually running various power-down self-tests automatically, without any user intervention. During power-down, the calibration intervals may be as frequent as every 1 millisecond, but may be as long as once every 1 week or once every 1 month. The calibration may last for some time period, such as 1 second, 1 minute, 1 hour, etc. during which time such time-dependent factors as offset drift can be estimated.

During these calibrations, such motion features as RMS noise, offset and drift may be estimated. The updated estimate of RMS noise can be used for determining the threshold for detection of the zero-velocity state. The updated estimates of offset and offset drift can be used to reduce the final positional accuracy to approximately 1% of the total distance traveled, e.g. for a typical clinical situation where the electrodes would move over 1.5 feet during placement, the error would be less than 0.25 inch.

By then tracking the relative spacing and relative angular orientation of the motion tracking sensors, the system can determine the hinging state of the envelope, (e.g. whether the envelope lying flat or is opened at a specific angle between the two halves of the envelope), or in the case of FIGS. 15 and 16, if one of the electrodes has been removed from the backing. In cases of ambiguity, for example if the defibrillator is turned on but it has not detected a separation occurring between the motion sensors promptly (after a few seconds) it will provide a prompt to the operator to "Open electrode package." If the defibrillator detects that the package is at least partially open but not laying flat, the system can provide a prompt to the operator to "Place Electrode Package on Flat Surface as Shown." Upon confirmation through input from the operator, the system can assume that the electrodes are collocated, and use tracking sensor signals at that point as an origin point for subsequent motion tracking calculations.

If the motion sensors are accelerometer-based, they will be able to measure gravitational force and direction. If the electrodes are substantially without motion and lying on the ground, gravitational force can be detected. If the envelope is open but not motionless or laying roughly orthogonal to gravitational force, then a prompt of speech/text/image may occur to indicate to "Lay the Electrodes Flat".

Other steps can be taken to establish the initial relative position of the electrodes. For example, the system may operate to issue a prompt to the user to place the electrodes, or the entire electrode package, in a particular arrangement, accept confirmation from the user that the electrodes have been placed in this arrangement, and the take the corresponding motion sensor signals as the origin for the electrodes. The system may prompt the user to open the envelope and the lay it flat, substantially horizontal and mark the resultant motion sensor signals as a particular motion state of the electrodes. In this case, that state is "Package open AND Package Laying Flat on Ground." The system can prompt the user to place the electrodes in other orientations, or prompt the user to accomplish other gestures, to establish an initial state of the electrodes. The state description may contain information about one or more aspects of motion such as position, velocity, acceleration, rotational attitude. In some embodiments, this state of stillness in relative motion between motion sensors may be used to re-calibrate the motion sensing, particularly positional information since the double integration of the accelerometer signal for inertial sensing can induce offsets and positional drift. The initial relative spacing between the motion sensors is known with the package open and laying flat and the electrodes still adhered to the inner wall of the envelope, and the defibrillator allows the relative spacing to stay that way in a calibrated state until a new "gesture" is detected. A "gesture," as used here, is any motion that results in a detectable change in either the relative motions (either velocity or acceleration) or position between the motion sensors which exceeds a predetermined threshold.

If both electrodes are detected to be laying flat at this point, the prompt is shown in FIG. 3, instructing the user to choose an electrode. Prompting as to correct placement may proceed as described above in relation to FIGS. 3 through 12.

Figure 4:
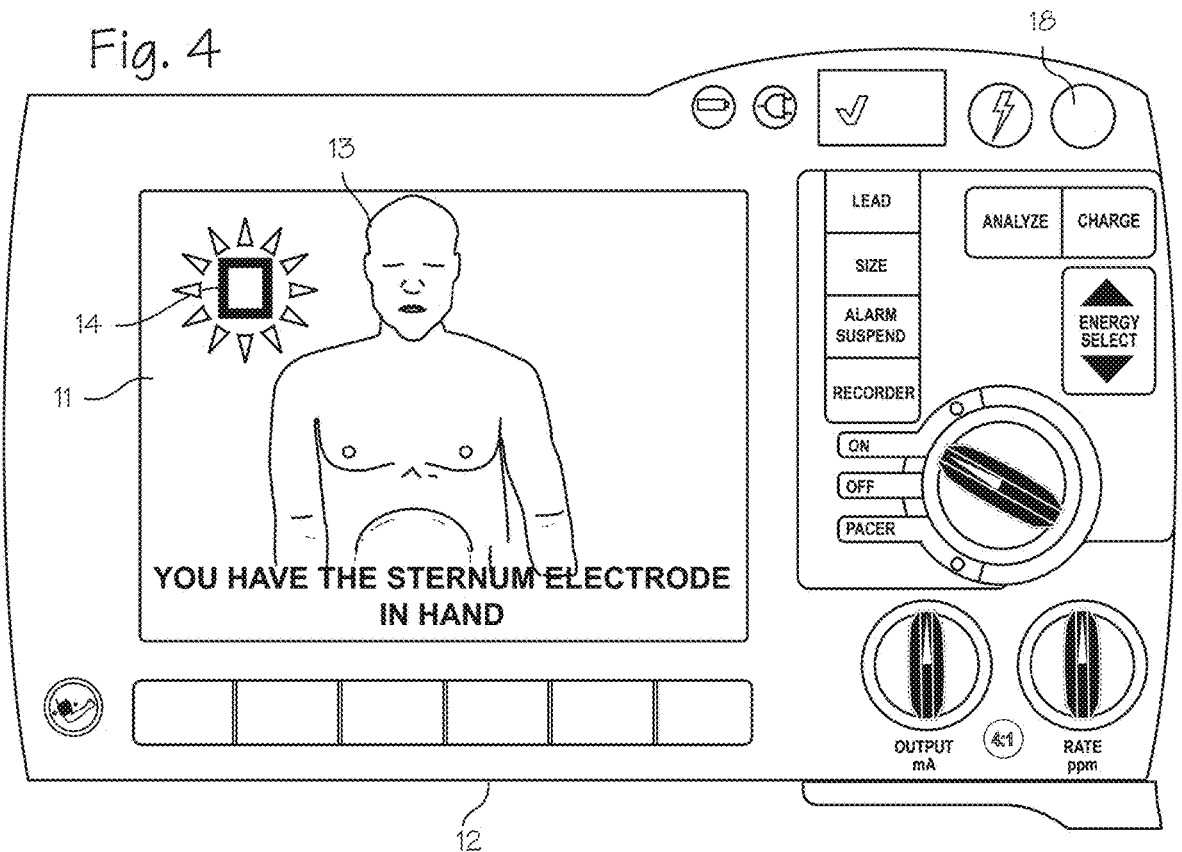

When one electrode is removed from its liner (i.e. a new "gesture" is detected), the relative motions or positions of the two motion sensors incorporated into the electrodes will diverge from the initial spacing and orientation of the electrodes. The other electrode, which remains in the carry envelope, will remain roughly horizontal while the first electrode is in motion. As described above, the system can readily detect which electrode has been taken by the user and removed from the envelope, and issue the prompt as shown in FIG. 4.

If the sternum electrode has been removed, the trajectory and orientation is tracked from the start of the sternum electrode's removal from the envelope. The defibrillator issues the audio or text prompt instruction, "Place the sternum electrode upper right" (FIG. 5) along with a static or moving image showing the exact location of the electrode on the body, with the electrode's relative location to anatomical landmarks like the collar bone or sternal notch or nipples. When either the movement of the sternum electrode's motion sensor has ceased or the relative motion compared to the apex electrode has ceased, then the prompt, "Confirm that sternum electrode is placed exactly as shown on display by tapping the electrode three times" is given, as shown in FIG. 6.

When the user taps on the electrode that has just been affixed to the patient, the tapping is detected by the motion sensor on that electrode and processed by the defibrillator. The detected tapping is used as an indication by the defibrillator that that gesture is complete and the sternum electrode is now in a state of "Sternum electrode attached to patient in the correct sternum location." Since the full path trajectory is known from the time of removal of the sternum electrode from the envelope until it is placed on the correct sternum location on the patient, the path back to the envelope is now known relative to the sternum location on the patient (as confirmed by the tapping gesture). Also, the system uses the motion tracking sensor data to determine the location and orientation of the electrode relative to the origin point. This can be depicted now on the defibrillator display.

Next, prompts are given to place the Apex electrode, as in FIG. 9. Because the location in three-dimensional space relative to the location of the already placed sternum electrode is known, the subsequent movement of the apex electrode, as it is pulled out of the envelope and moved to the intended location of the patient, may now be depicted on the defibrillator display in real time as the action is occurring. The system uses the tracking sensor signals to determine the motion of the apex electrode, and calculate position and orientation of the apex electrode relative to the origin, and thus relative to the previously placed electrode.

Figure 17:
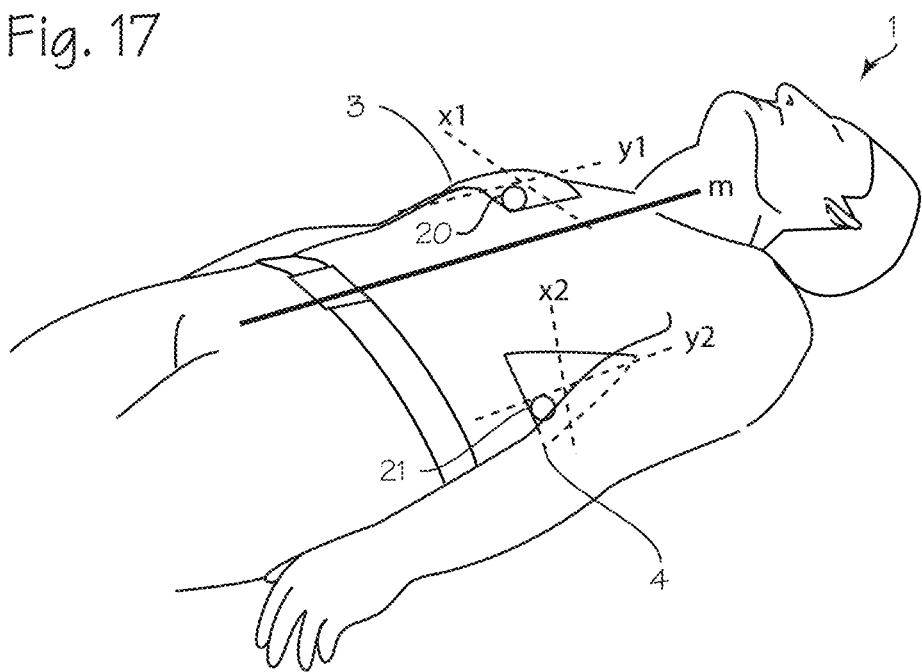
FIG. 17 illustrates the preferred placement of apex and sternal electrodes on the body of a patient.

With the relative locations and orientations of the electrodes determined through the motion tracking system, the control system can accomplish several functions. As illustrated in FIG. 17, the motion tracking sensor 20 associated with sternum electrode 3 should, though disposed on the body, be lying roughly flat, in a plane (x1,1) close to parallel to the plane defined by the ground, or the anterior surface of the patient's chest, perhaps tilted downwards toward the superior direction (toward the clavicle) and the medial direction (toward the right armpit). The motion tracking sensor 21 associated with apex electrode 4 should lie in a distinctly different plane (x2,y2), if properly positioned as shown in FIG. 17. To confirm that the electrodes are properly placed, the control system calculates the location and orientation of each electrode, compares the orientation, and determines if the orientation of the electrodes is within predetermined ranges. (Initially, the predetermined range may be 15° or greater angular difference between the plane of each motion tracking sensor assembly, which will indicate that the orientation is sufficiently distinct to confirm that the apex electrode is not placed too far toward the mid-line of the patient.) If not, the system can issue prompts to the user, seeking additional input confirming proper location or suggesting relocation of one of the electrodes. If the original position determination was made pursuant to a prompt to place the electrodes on the ground or other horizontal plane, the system can also compare the orientation of each electrode to the horizontal or vertical, and determine if the electrodes are oriented properly relative to horizontal and vertical (the sternum electrode should be parallel to the horizontal, while the apex electrode should be at a significant angle to the horizontal, approaching vertical, depending on the location of the small motion tracking sensor assembly on the apex electrode. Again, if not, the system can issue prompts to the user, seeking additional input confirming proper location or suggesting relocation of one or both of the electrodes.

In addition to determining relative angle between the two motion tracking sensor assemblies 20 and 21, the system can determine the distance between each electrode, and, if outside predetermined limits, prompt the user to confirm proper placement or relocate the one or both of the electrodes. For example, if properly placed, the electrodes should not be closely aligned relative to the medial axis of the patient's body (line m in FIG. 17). Thus, the system can be programmed to determine the lateral separation of the electrodes, and, if outside predetermined parameters, issue prompts to the user, seeking additional input confirming proper location or suggesting relocation of one or both of the electrodes.

Each of the techniques can be used to guide and confirm placement of electrodes in the anterior-posterior or anterior-apex placement schemes, and other schemes that apply to two electrode defibrillator systems or multi-lead diagnostic system.

With the location and orientation of each electrode determined, and proper placement confirmed, the location and orientation data can be used to estimate the size of the patient The system can estimate the weight, chest dimensions and other anatomic characteristics of the patient, using the relative positional and orientation information along with population-based anthropometric data.

If the relative positions and orientation do not match any anthropometric data, or even if it is statistically improbable given the population characteristics for that measurement parameter, the system will issue a prompt to the user to confirm placement of the electrodes, either with a manual input through the defibrillator or through a gesture such as tapping one or both of the electrodes.

Once patient size has been estimated, then therapy can be customized based on this estimation. The amount of defibrillation energy can also be adjusted based on those estimates. For example, large patients will require higher defibrillation currents to successfully defibrillate. Typical current requirements for defibrillation are 10 to 15 amperes for the first phase average current, but for very large patients, this may be insufficient, and delivery of shock at 20 amperes of current is more likely to be effective. In terms of energy levels, the initial defibrillation shock energy for a smaller patient may be approximately 100-150 J; for larger patients, the initial defibrillation shock energy may be 200 J.

If the estimated patient size is large (e.g., adult of 80-100 kg), the system may prompt the user to deliver CPR compressions during the course of CPR resuscitation to deliver compressions that are 3 inches deep, instead of the currently-recommended Guideline from the AHA of 2 inches. This 2 inch Guideline was chosen by the scientific members of the Guidelines committee as the best guess of the average depth across all patient sizes, knowing that optimal depth varied across the patient population. Or, if the system determines that the estimated patient size is small (e.g., child of 10-30 kg), the system may prompt the user to deliver CPR chest compressions that are less than 2 inches, for example, 1-1.5 inches. If the system is used in conjunction with an automatic chest compression device, the size determined can be used as input to control the automated chest compression device, to provide deeper compressions for larger patient, or shallower compressions for a smaller patient.

The adjustments to compression depth, defibrillation energy or other therapeutic parameter can be adjusted based on a stored relationship between the estimated anthropometric parameter and the therapeutic parameter. The relationship can be a linear or non-linear equation stored in memory on the defibrillator. The relationship can be stored as a table look-up. The relationship can be derived by various statistical regression methods of optimization.

Various additional features can be added to the system described above. Additional motion sensors may be located on the carry envelope to detect motion of the electrodes relative to the envelope. In this way, it can be more easily determined that the electrodes have been removed from the envelope. There may be an additional relative motion sensing between the defibrillator housing and the envelope that, when detected, will automatically turn the defibrillator on, or transition the defibrillator electronics from a lower power stand-by state to a state of normal operation and clinical mode. A magnet may be integrated in the carry envelope, and magnetic relay disposed on the defibrillator. When the envelope is attached to the side of the defibrillator, the magnetic flux may activate the magnetic relay located inside the defibrillator housing, adjacent to the location of the magnet. When the envelope is removed from the side of the defibrillator, the relay is de-activated which then causes a voltage pulse that is used as an interrupt to a micro-power real-time clock circuit with an interrupt wake-up function. Alternatively, the relay can be replaced with a coil that generates a voltage pulse when the envelope is removed and the magnet is pulled away from its location, due to the changing magnetic flux.

Alternatively, the magnet/coil arrangement can be integrated into the hinged envelope arrangement, so that the unit will automatically turn on when the envelope is opened.

Alternatively, a separate, ultra-low-power processor in the defibrillator may be dedicated to processing the motion sensor data. This motion processor will run even when the defibrillator is in the "OFF" state—when it is either in stand-by, non-clinical mode or with the display off. When the motion processor detects the envelope being moved or opened, in some embodiments, it may turn the defibrillator "ON"—e.g. send an interrupt to the main processor to turn the display on and transition the defibrillator operation to normal clinical operational mode.

The motion sensor may be based on magnetic induction or by laser interferometry such as ring laser gyro Honeywell GG1320AN. The motion tracking system may also be implemented with magnetic field generator similar to that disclosed in Centen, et al., *Reference Sensor For CPR Feedback Device*, U.S. Pub. 2012/0083720 (Apr. 5, 2012), with a magnetic field generator disposed within the defibrillator or otherwise for example in separate paddle disposed under the patient as illustrated in *Centen*, and magnetic field sensors disposed on each electrode (or vice-versa), with corresponding programming in the control system to use motion data derived from motion through the magnet field sensors to track the motion, placement and orientation of the electrodes, and use that information as described above.

The system described above can be implemented with an additional motion sensor disposed on the sternum of the patient, where the hands are pressed for CPR compressions. This additional motion sensor may take the form of a "puck" with indicia indicating the proper point for applying manual compressions, or may be a piece of self-adhesive foam in a similar configuration as the puck. In both cases, the motion sensing is integrated into that element. The bottom end of adhering element may have anatomical markings printed on it depicting the sternal notch. The motion sensor is located 2" (or whatever is the optimal clinical location) up from sternal notch. That same motion sensor can then be used also to measure compression depth. The motion of both the motion tracking sensors in the electrodes as well as the motion sensor of the sternum pad is tracked during compressions to create a full three-dimensional view of the biomechanics of chest wall motion during chest compressions to further optimize compressions for each patient. For instance, barrel chested patients may have stiffer chests that show less movement of the ribs during compressions, and a prompt may be given to increase compression depth or even to alter the location of the caregiver's hands to a position closer to the sternal notch, to increase the leverage.

The same system used in the ECG monitor or AED to control the ECG analysis and shock generation functions of those devices, as described above, may be used to analyze the motion signals and motion tracking signals, and generate and deliver prompts to the technician. Alternatively, a separate control system, comprising a separate computer, may be used to receive and analyze electrode motion sensor signals and motion tracking signals, and operate the user communications devices to issue prompts. The various functions may be performed by either processor. In either case, the system comprises at least one processor and at least one memory including program code, with the memory and computer program code configured with the processor to cause the system to perform the functions described throughout this specification.

Various ranges and thresholds expressed above are sufficient to determine electrode motion, relative motion, and relative position and orientation to the accuracy needed or helpful in prompting placement or seeking confirmation from the technician. These thresholds may be varied, and may be altered as clinical experience dictates, or according to the manufacturer's desired degree of certainty or uncertainty in electrode movement and placement which warrants a prompt.

Figure 18:
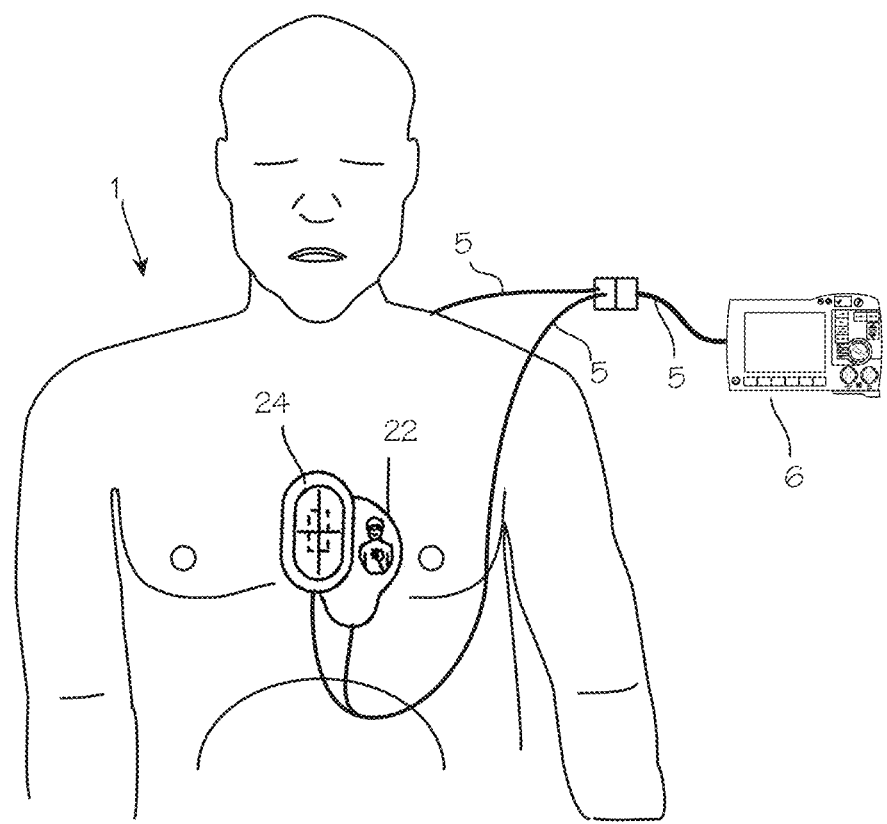
FIGS. 18 and 19 illustrate and anterior-posterior electrode placement useful with the motion tracking system.
Figure 19:
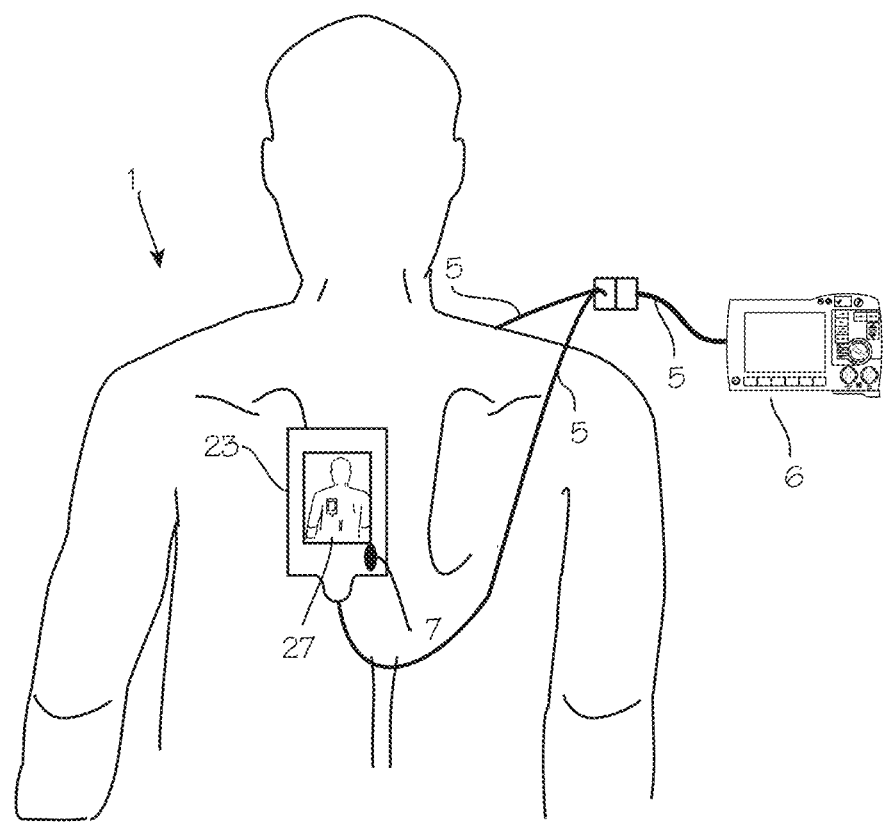
Figure 20:
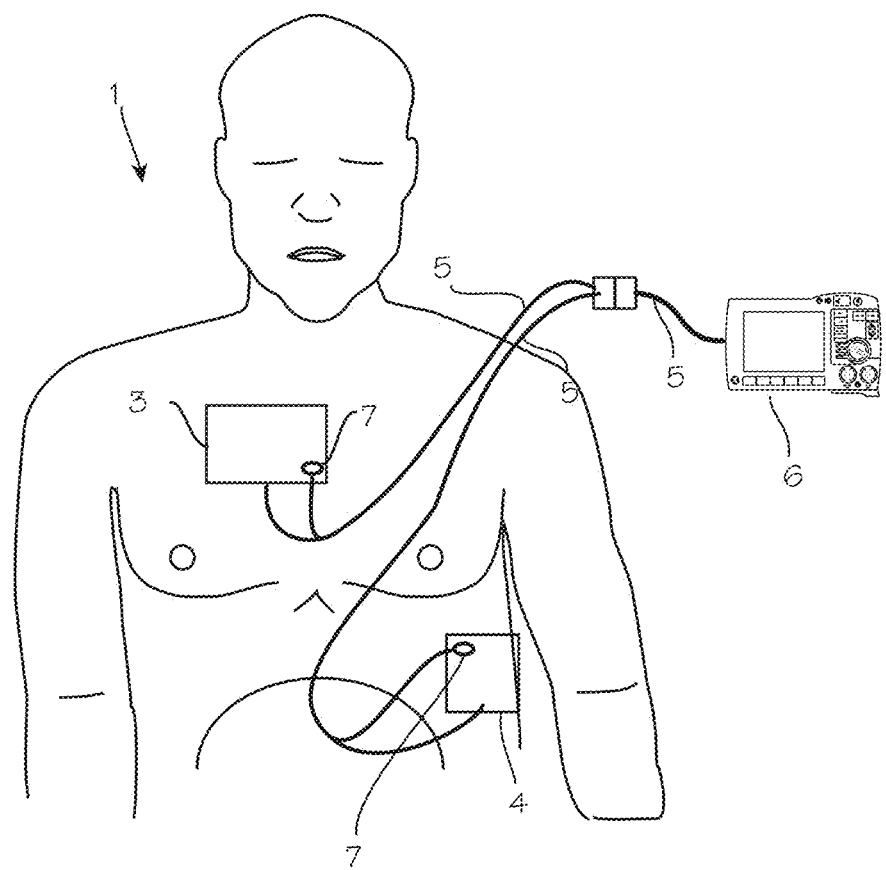
FIG. 20 illustrates an anterior-anterior electrode placement useful with the motion tracking system.

In certain examples, such as those illustrated in FIGS. 18 and 19, the resuscitation system of this disclosure includes electrode assemblies, with chest compression sensors secured to one or both of the electrode pads. As shown in FIGS. 18 and 19, one electrode assembly may be placed at an anterior position (e.g., over the sternum) of the patient and a second electrode assembly may be placed on a posterior position (e.g., on the back, opposite the anterior placed electrode) of the patient, i.e., in an A-P placement. Alternatively, as illustrated in FIG. 20, a first electrode assembly may be placed on an anterior position (the sternal position) of the patient and a second resuscitation electrode assembly may be placed on a side position (the apex position) of the patient, i.e., in an A-A placement. In such a context, it may be advantageous to be able to track the movement of each of the electrode assemblies while coupled to the patient.

By incorporating chest compression and/or motion sensors in both electrode assemblies, resuscitation related parameters may be more accurately determined than would otherwise be the case if only one electrode assembly incorporated a motion sensor. For instance, the electrode assemblies may serve as reference points for one another, based on their respective displacement and orientation. Accordingly, the manner in which the electrode assemblies (e.g., electrode pads) are placed and/or how they move relative to one another may inform the type of instructions output to a rescuer. As an example, based on their orientation and/or distance relative to one another, it can be determined whether the electrode assemblies are placed in an A-A or A-P placement, or not in any recommended position at all. In addition, based on the pattern of movement of both electrode assemblies, the type of surface on which the patient resides can be determined, or the angle with respect to the vertical axis (when the patient is lying down) at which chest compressions are being administered can also be estimated.

FIGS. 18 and 19 illustrate an anterior-posterior electrode placement useful with the motion tracking system described above. As shown in FIGS. 18 and 19, the resuscitation assembly includes an anterior electrode 22 and a posterior electrode 23 placed on a patient 1. The patient 1 is shown with the anterior electrode assembly 22 secured to the anterior surface of the patient's chest, and the posterior electrode 23 secured to the patient's back an anterior-posterior (A-P) configuration. The sensor associated with the anterior electrode 22 may be provided as a chest compression monitor 24 as depicted in FIG. 18.

FIG. 20 illustrates an anterior-anterior electrode placement useful with the motion tracking system described above. As shown in FIG. 20, a sternal electrode assembly 3 and an apex electrode 4 of the resuscitation assembly are positioned on the patient in an A-A orientation, with the sternal electrode assembly 3 is positioned on a right side of a chest of the patient 1 between the armpit and the sternum, with the portion of the electrode assembly comprising the motion sensor 7 placed substantially above the sternum. The apex electrode assembly 4 is positioned on the left side of the chest of the patient 1 over lower ribs of the patient 1. In either configuration, the motion sensors 7 of the electrode assemblies 22, 23, 3, and 4 may be provided as three-axis accelerometers as described above, such that acceleration in the x, y, and z directions is measured simultaneously with each of two sensors incorporated within respective electrode assemblies.

The resuscitation assemblies of FIGS. 18, 19 and 20 are illustrated as operatively connected to a defibrillator 6, such as a ZOLL Medical R Series, X Series Monitor Defibrillator, or any other defibrillation system, which can operate as an AED, a semi-automatic defibrillator (SAD), and/or a manual defibrillator with a monitor, and can also be used for cardioverting and pacing, through cables 5. The defibrillator 6 is operable to generate a defibrillating shock and deliver that shock to the patient through the electrode assemblies. In one example, the defibrillator 6 can include an ECG monitor and display for analyzing the ECG signals obtained through the electrode pad and displaying the ECG waveform to a user. The display can also provide the user with feedback regarding chest compressions as disclosed in Tan, et al, *Defibrillator Display*, U.S. Pat. No. 9,289,134 (Mar. 22, 2016), which is hereby incorporated by reference in its entirety.

The system is programmed to receive and process the motion signals from the motion sensors to determine whether a patient is being transported or not. For instance, if the acceleration signals are associated with patient transport, the system may instruct a rescuer to take steps to ensure that the patient is properly secured. Once the patient is suitably secured, the system may instruct the user to administer chest compressions, or another resuscitation activity. Or, when rescuers are subject to a scoring system that evaluates their performance (e.g., report card) in carrying out resuscitation activities, if it is determined that the patient is being transported, the metrics for evaluating the rescuer may be adjusted. For instance, performing manual chest compressions while traveling in an ambulance may be more difficult than when not located in a traveling vehicle, and so the rescuer may be given a score that reflects such conditions. That is, to account for the rescuer being subject to conditions where it is more challenging to administer CPR or when CPR quality is likely to be compromised, such as during vehicular motion or transport, the manner in which a rescuer is evaluated may be relaxed and the overall performance evaluation may be higher. Or, for purposes of evaluating rescuer performance, CPR measurements during transport may be discounted from the overall score. Thus, the scoring rubric for assessing the rescuer may account for whether chest compressions are being administered during transport.

In addition, the system may be further programmed to alert a user when there is concern for rescuer safety, through, for example, a communication device. For example, when a substantial amount of vehicle/transport motion is detected, to ensure that the rescuer does not become injured or become a potential liability (being a large object that can move suddenly within and throughout the vehicle cabin) for other passengers, it may be preferable for the rescuer to discontinue CPR and rather be placed under a safety restraint (e.g., seat-belt).

In addition, when electrode assemblies comprising one or more motion sensors in each are placed in the A-P placement, with one electrode in front and one electrode on the back of the patient, oriented substantially parallel to one another (that is, a plane defined by the general orientation of one electrode is parallel to a plane established by the general orientation of the other electrode), and the patient is lying on a compressible surface such as a mattress or thick padding, the system to which the electrode assemblies are connected may accurately estimate the depth of chest compressions during CPR by subtracting out the distance traveled by the posterior placed assembly. When such electrode assemblies are placed in an A-A placement (front and side), oriented substantially perpendicular to one another (that is, a plane defined by the general orientation of one electrode is perpendicular to a plane established by the general orientation of the other electrode), rather than the subtraction technique described herein, the system may employ a different algorithm for estimating the depth of chest compressions. For instance, when recognizing pads placed in an A-A position, for purposes of estimating the depth of chest compressions, the system may elect to process data received from only the motion sensor positioned on the front of the patient without data from the motion sensor positioned on the side of the patient. Otherwise, inaccuracies may arise when the wrong correction algorithm is used, for example, using an algorithm corresponding to A-P pad placement when in fact the pads are placed in an A-A position.

The system may recognize that electrode assemblies have been placed in an A-A position when the separate motion sensors are oriented relative to one another at an angle greater than a threshold angle. For example, electrode assemblies oriented substantially perpendicular to one another may be considered to be in an A-A position. Conversely, it may be recognized that electrode assemblies are placed in an A-P position when the separate motion sensors are oriented relative to one another at an angle greater than the threshold angle. Hence, electrode assemblies oriented substantially parallel to one another may be considered to be in an A-P position. In various embodiments, the threshold angle is about 30 degrees, about 40 degrees, about 50 degrees, or about 60 degrees.

The overall orientation of the patient may also be determined no matter what the orientation is of the sensor(s). For instance, even if one of the sensors is misplaced or tilted in an otherwise undesirable manner, the anterior/posterior axis of the patient (direction perpendicular to the surface of the chest) may be determined by comparing the movement and/or position of the two sensors relative to one another.

FIG. 21 is a flow chart illustrating this method of controlling the method of compression depth calculation based on determined electrode placement. First, the rescuer positions the electrode assemblies 22 and 23 (placed in A-P placement) or electrode assemblies 3 and 4 (placed in A-A placement) on the patient (see block 25). Once the electrode assemblies are placed on the patient, a signal is obtained from each motion sensor 7 to provide a baseline acceleration of gravity (see block 26). By measuring the baseline acceleration of gravity, the system determines the initial orientation of each motion sensor of the electrode assemblies and rotates the reference sensor (i.e., motion sensor 7 of the electrode assembly positioned anteriorly or posteriorly) to the same plane as the primary sensor (i.e., motion sensor 7 positioned anteriorly on the patient's sternum). This process reduces errors caused by a non-parallel alignment of the primary and reference sensors. In addition, the baseline accelerations measured by the reference sensor can be used to determine whether the reference sensor was placed posteriorly or anteriorly (see block 27). If an anterior placement is used for the reference sensor (see the configuration of 20), the accelerations detected by the motion sensor 7 of resuscitation assembly 4 (i.e., the reference sensor) are disregarded and compression depth is determined solely based on a signal from motion sensor 7 of electrode assembly 3 (i.e., the primary sensor as discussed hereinabove (see block 28)). If a posterior placement is used for the reference sensor (see the configuration of FIGS. 16 and 17), the chest compression depth is calculated by subtracting a distance traveled by the motion sensor of the electrode assembly 23 (i.e., the secondary sensor) from a distance traveled by the motion sensor of the electrode assembly 22 (i.e., the primary sensor) as described hereinabove (see block 29).

One challenge in using two motion sensors such as motion sensors 7 of electrode assemblies 22 and 23 or 3 and 4, for example, is that the two sensors may not be in the same orientation. By measuring acceleration in three dimensions, when the motion sensors 7 are configured as three-axis accelerometers, it is possible to determine a baseline orientation of each motion sensor 7 and then rotate the reference sensor (i.e., the motion sensor 7 of the resuscitation assembly 23) to be in the same plane as the primary sensor (i.e., the motion sensor 7 of the resuscitation assembly 22).

For certain cases, the rotation of a baseline vector of each motion sensor 7 may be determined by averaging a quiet period with no movement. From these vectors angles ($\alpha$, $\beta$, $\gamma$) between the primary and reference sensors are calculated. A rotation matrix is then calculated to first rotate the reference vector around the Z-axis by an angle $\gamma$ (see Equation 1 below) and then rotate the vector again around the X-axis by an angle $\alpha$ (see Equation 2 below). Each measurement on the reference sensor is multiplied by the rotation matrix $R_x R_z$.

$$R_z = \begin{bmatrix} \cos(\gamma) & -\sin(\gamma) & 0 \\ \sin(\gamma) & \cos(\gamma) & 0 \\ 0 & 0 & 1 \end{bmatrix} \quad \text{Equation 1}$$

$$R_x = \begin{bmatrix} 1 & 0 & 0 \\ 0 & \cos(\alpha) & -\sin(\alpha) \\ 0 & \sin(\alpha) & \cos(\alpha) \end{bmatrix} \quad \text{Equation 2}$$

After the rotation is performed, the compression depth is calculated using the acceleration component as measured in the direction perpendicular to the chest surface (e.g., y-axis acceleration) from the primary and reference sensor. The depth is calculated by subtracting the acceleration in the direction perpendicular to the chest surface as detected by the motion sensor 7 of the resuscitation assembly 23 placed posteriorly on the patient 1 from the acceleration in the direction perpendicular to the chest surface as detected by the motion sensor 7 of the electrode assembly 22 placed anteriorly on the patient 1.

Alternatively, a rotation calibration may be performed via a normalized cross product calculation, such as that described in Kovacs, *Rotation About An Arbitrary Axis And Reflection Through An Arbitrary Plane*, 40 Annales Mathematicae et Informaticae 175 (2012). In this method, to perform the rotation calibration, the baseline vector of each sensor is determined by averaging a quiet period with no movement. To rotate one vector to another, the vectors are first transformed so the axis of rotation is coordinate with the Z-axis. A rotation around the Z-axis of the angle between the two vectors is then performed and the inverse of the transformation is applied to the vectors. The axis of rotation is the normalized cross product of the reference sensor vector and the primary sensor vector.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A resuscitation system for aiding a user in providing a resuscitative treatment to a patient, said system comprising:
a first electrode with a first accelerometer disposed in fixed relation to the first electrode within a package;
a second electrode with a second accelerometer disposed in fixed relation to the second electrode within the package; and at least one processor, with memory, power supply and other processing components, the at least one processor configured to analyze motion signals by comparing differences between at least one of acceleration and velocity signals from the first and second accelerometers to determine the location and orientation of the first and second electrodes relative to each other, and determine whether the first and second accelerometers are packaged together, removed from the package and moving, or removed from the package and stationary; and a communication component configured to provide at least one prompt that includes guidance for assisting the user in placement of at least one of the first electrode and the second electrode on the body of the patient.

2. The system of claim 1, wherein the communication component is configured to provide at least one prompt based on the analyzed motion signals to assist the user in providing the resuscitative treatment to the patient.

3. The system of claim 2, wherein the at least one prompt includes at least one of a visual display, an image, a moving image, visual instructions, visual text, verbal audible instructions and non-verbal audible instructions.

4. The system of claim 2, wherein the at least one prompt includes guidance for assisting the user in confirming placement of at least one of the first electrode and the second electrode on the body of the patient.

5. The system of claim 4, wherein the at least one processor is configured to detect whether placement of at least one of the first electrode and the second electrode on the body of the patient has been confirmed based on the analyzed motion signals.

6. The system of claim 5, wherein the confirmation of placement of at least one of the first electrode and the second electrode involves detection of a manipulation by the user of the respective electrode.

7. The system of claim 2, wherein the at least one processor is configured to estimate a size of the patient based on the determined location and orientation of the first and second electrodes relative to each other.

8. The system of claim 7, wherein the at least one processor is configured to provide a chest compression signal based on the estimated size of the patient for providing chest compressions to the patient.

9. The system of claim 8, wherein the chest compression signal results in a prompt for providing guidance to the user relating to administration of at least one a preferred chest compression depth and a preferred chest compression rate.

10. The system of claim 7, wherein the at least one processor is configured to provide a defibrillation energy signal based on the estimated size of the patient for administering a level of defibrillation energy to the patient.

11. The system of claim 7, wherein the at least one processor is configured to provide a ventilation signal based on the estimated size of the patient for providing ventilations to the patient.

12. The system of claim 11, wherein the ventilation signal results in a prompt for providing guidance to the user relating to administration of at least one of a preferred ventilation tidal volume and a preferred ventilation minute volume.

13. The system of claim 7, comprising: a defibrillator operable to deliver a shock to a patient through the first and second electrodes; wherein the at least one processor is configured to control delivery of the shock based on the estimated size of the patient.

14. The system of claim 2, wherein: the at least one processor is configured to issue a prompt to the user if the orientation deviates from a predetermined orientation corresponding to an electrode placement scheme suitable for ECG analysis.

15. The system of claim 2, wherein: the at least one processor is configured to issue a prompt to the user if the orientation deviates from a predetermined orientation corresponding to an electrode placement scheme suitable for delivery of shock to the patient.

16. The system of claim 2, wherein: the at least one processor is configured to a prompt to the user if the distance between the electrodes deviates from a predetermined distance corresponding to an electrode placement scheme suitable for ECG analysis.

17. The system of claim 2, wherein: the at least one processor is configured to issue a prompt to the user if the distance between the electrodes deviates from a predetermined distance corresponding to an electrode placement scheme suitable for delivery of shock to the patient.

18. The system of claim 2 wherein the at least one processor is configured such that, upon determining the location of the first and second electrodes relative to each other, the at least one processor will send a signal to operate the communication component to (1) issue a prompt to the user to relocate the first electrode or second electrode or, conditionally, (2) issue a prompt to the user to perform a gesture which generates motion signals in order to confirm location of one of the first and second electrodes.

19. The system of claim 2 wherein the at least one processor is configured operate the communication component to (1) issue a prompt to the user to perform an initial gesture with the first and second electrodes and associate the detection of the initial gesture with an origin of the first and second electrodes and thereafter determine relative location of the first and second electrodes based on the origin of the first and second electrodes.

20. The system of claim 2, comprising a defibrillator operable to deliver shock to a patient through the first and second electrodes, wherein the at least one processor, with memory, power supply and other processing components and the communication component are part of the defibrillator.

21. The system of claim 2, comprising a defibrillator operable to deliver shock to a patient through the first and second electrodes, wherein the at least one processor, with memory, power supply and other processing components are part of the defibrillator and the communication component is part of a device separate from the defibrillator.

22. The system of claim 1, wherein the at least one prompt includes an image of a patient indicating a preferred location for the user to place at least one of the first electrode and the second electrode on the body of the patient.

23. The system of claim 22, wherein the at least one prompt includes an image indicating the determined location of the first and second electrodes relative to each other.

24. The system of claim 1, wherein upon a determination that the first and second accelerometers are packaged together or removed from the package and stationary, the at least one processor is configured to calibrate measurements of the acceleration or velocity to estimate and compensate for at least one of RMS noise, offset and drift.

25. The system of claim 1, wherein the at least one prompt is based on the determined location and orientation of the first and second electrodes relative to each other to assist the user in placement of at least one of the first electrode and the second electrode on the body of the patient.

26. A resuscitation system for aiding a user in providing resuscitative treatment to a patient, said system comprising:
an electrode with a accelerometer disposed in fixed relation to the electrode within a package;
a communication component operable to issue placement prompts to the user;
at least one processor, with memory, power supply and other processing components, the at least one processor configured to
analyze motion signals from the accelerometer to determine whether the electrode is removed from the package and moving or removed from the package and stationary, and
in response to a determination that the accelerometer is removed from the package and moving, operate the communication component to provide at least one prompt based on the analyzed motion signals to assist the user in providing the resuscitative treatment to the patient; and
wherein the at least one prompt is provided to assist the user in placing the electrode on the body of the patient.

* * * * *